(12) United States Patent
Bjäre et al.

(10) Patent No.: US 11,516,183 B2
(45) Date of Patent: Nov. 29, 2022

(54) MEDICAL DEVICE SYSTEM INCLUDING INFORMATION TECHNOLOGY INFRASTRUCTURE HAVING SECURE CLUSTER DOMAIN SUPPORTING EXTERNAL DOMAIN

(71) Applicant: GAMBRO LUNDIA AB, Lund (SE)

(72) Inventors: Björn Bjäre, Lund (SE); Roland Persson, Limhamn (SE)

(73) Assignee: Gambro Lundia AB, Lund (SE)

( * ) Notice: Subject to any disclaimer, the term of this patent is extended or adjusted under 35 U.S.C. 154(b) by 568 days.

(21) Appl. No.: 16/472,090

(22) PCT Filed: Dec. 7, 2017

(86) PCT No.: PCT/EP2017/081763
§ 371 (c)(1),
(2) Date: Jun. 20, 2019

(87) PCT Pub. No.: WO2018/114346
PCT Pub. Date: Jun. 28, 2018

(65) Prior Publication Data
US 2020/0092259 A1 Mar. 19, 2020

(30) Foreign Application Priority Data
Dec. 21, 2016 (SE) .................... 16516999

(51) Int. Cl.
*G06F 16/28* (2019.01)
*H04L 9/40* (2022.01)
*G16H 40/67* (2018.01)

(52) U.S. Cl.
CPC ........ *H04L 63/0272* (2013.01); *G06F 16/285* (2019.01); *G16H 40/67* (2018.01)

(58) Field of Classification Search
None
See application file for complete search history.

(56) References Cited

U.S. PATENT DOCUMENTS 250,868 A 12/1881 Abbott
927,476 A 7/1909 Barker
(Continued)

FOREIGN PATENT DOCUMENTS

CH 296007 1/1954
DE 1806654 5/1970
(Continued)

OTHER PUBLICATIONS

International Search Report for corresponding International Application PCT/US2009/031809 dated Oct. 19, 2009.
(Continued)

*Primary Examiner* — Cai Y Chen
(74) *Attorney, Agent, or Firm* — K&L Gates LLP

(57) ABSTRACT

A medical device information technology ("IT") data transfer system in one embodiment includes a cluster domain, an external domain and an interface domain. Equipment belonging to the cluster domain may communicate in real time such that availability, safety, security, reliable integrity and performance are guaranteed. The external domain includes equipment not enabled for direct inclusion in the cluster domain, and may include equipment for external information systems, presentation equipment, personal computer equipment, shared medical equipment and bedside medical equipment. The interface domain enables external domain equipment to communicate with cluster equipment in a bidirectional manner. Communication may be via certain access nodes in the cluster. The access nodes enable exchange of information between the open external domain and the closed and private cluster domain.

20 Claims, 12 Drawing Sheets

(56) References Cited

U.S. PATENT DOCUMENTS

| | | |
|---|---|---|
| 1,505,050 A | 8/1924 | Lauritsen |
| 2,292,007 A | 8/1942 | Morgan |
| 2,529,028 A | 7/1947 | Landon |
| 2,122,509 A | 7/1948 | Beliaeff |
| 2,736,332 A | 2/1956 | Simmons |
| 3,044,236 A | 7/1962 | Bearden et al. |
| 3,074,645 A | 1/1963 | Main |
| 3,095,062 A | 6/1963 | Neely |
| 3,229,445 A | 1/1966 | Kraft |
| 3,287,885 A | 11/1966 | Sommer |
| 3,295,297 A | 1/1967 | Collins |
| 3,332,737 A | 7/1967 | Krause |
| 3,342,019 A | 9/1967 | Smythe |
| 3,388,803 A | 6/1968 | Scott |
| 3,412,760 A | 11/1968 | Franck |
| 3,426,150 A | 2/1969 | Tygart |
| 3,463,728 A | 8/1969 | Kolobow et al. |
| 3,485,245 A | 12/1969 | Lahr et al. |
| 3,490,479 A | 1/1970 | Mott et al. |
| 3,527,572 A | 9/1970 | Urkiewicz |
| 3,528,550 A | 9/1970 | Cappelen Jr. |
| 3,540,477 A | 11/1970 | Hogel |
| 3,545,438 A | 12/1970 | De Vries |
| 3,563,381 A | 2/1971 | Edelson et al. |
| 3,581,464 A | 6/1971 | Bhuta et al. |
| 3,598,727 A | 8/1971 | Wilock |
| 3,608,729 A | 9/1971 | Haselden |
| 3,617,545 A | 11/1971 | Dabois et al. |
| 3,619,423 A | 11/1971 | Galletti et al. |
| 3,667,612 A | 6/1972 | Leonard |
| 3,669,878 A | 6/1972 | Marantz et al. |
| 3,669,880 A | 6/1972 | Marantz et al. |
| 3,677,710 A | 7/1972 | Hirsch |
| 3,682,817 A | 8/1972 | Marx |
| 3,685,680 A | 8/1972 | Tenckhoff et al. |
| 3,697,418 A | 10/1972 | Johnson |
| 3,703,959 A | 11/1972 | Raymond |
| 3,707,967 A | 1/1973 | Kitrilakis et al. |
| 3,727,612 A | 4/1973 | Sayers et al. |
| 3,730,183 A | 5/1973 | Goldsmith et al. |
| 3,739,943 A | 6/1973 | Williamsen et al. |
| 3,742,938 A | 7/1973 | Stern |
| 3,744,492 A | 7/1973 | Leibinsohn |
| 3,744,636 A | 7/1973 | Commarmot |
| 3,756,234 A | 9/1973 | Kopp |
| 3,756,752 A | 9/1973 | Stenner |
| 3,769,207 A | 10/1973 | Baer |
| 3,771,288 A | 11/1973 | Wisman et al. |
| 3,774,762 A | 11/1973 | Lichtenstein |
| 3,786,190 A | 1/1974 | Pori |
| 3,795,088 A | 3/1974 | Esmond |
| 3,799,873 A | 3/1974 | Brown |
| 3,809,241 A | 5/1974 | Alvine |
| 3,809,871 A | 5/1974 | Howard et al. |
| 3,810,102 A | 5/1974 | Parks, III et al. |
| 3,814,249 A | 6/1974 | Eaton |
| 3,825,493 A | 7/1974 | Brown et al. |
| 3,827,561 A | 8/1974 | Serfass et al. |
| 3,827,975 A | 8/1974 | Bizot et al. |
| 3,830,234 A | 8/1974 | Kopp |
| 3,834,386 A | 9/1974 | Sisley |
| 3,848,112 A | 11/1974 | Weichselbaum et al. |
| 3,849,071 A | 11/1974 | Kayser |
| 3,850,835 A | 11/1974 | Marantz et al. |
| 3,858,574 A | 1/1975 | Page |
| 3,878,095 A | 4/1975 | Frasier et al. |
| 3,878,564 A | 4/1975 | Yao et al. |
| 3,884,808 A | 5/1975 | Scott |
| 3,908,653 A | 9/1975 | Kettering |
| 3,910,257 A | 10/1975 | Fletcher et al. |
| 3,911,915 A | 10/1975 | Seifter et al. |
| 3,915,802 A | 10/1975 | Kominek |
| 3,910,260 A | 11/1975 | Sarnoff et al. |
| 3,921,196 A | 11/1975 | Patterson |
| 3,926,797 A | 12/1975 | Gigou et al. |
| 3,939,069 A | 2/1976 | Granger et al. |
| 3,946,731 A | 3/1976 | Lichtenstein |
| 3,964,479 A | 6/1976 | Boag et al. |
| 3,971,000 A | 7/1976 | Cromwell |
| 3,976,311 A | 8/1976 | Spendlove |
| 3,979,284 A | 9/1976 | Granger et al. |
| 3,985,134 A | 10/1976 | Lissot et al. |
| 3,989,622 A | 11/1976 | Marantz et al. |
| 3,996,027 A | 12/1976 | Schnell et al. |
| 3,998,103 A | 12/1976 | Bjorklund et al. |
| 4,000,072 A | 12/1976 | Sato et al. |
| 4,031,010 A | 6/1977 | Nose |
| 4,031,891 A | 6/1977 | Jess |
| 4,032,908 A | 6/1977 | Rice et al. |
| 4,036,747 A | 7/1977 | Hori et al. |
| 4,038,190 A | 7/1977 | Baudet et al. |
| 4,047,563 A | 9/1977 | Kurata |
| 4,048,995 A | 9/1977 | Mittleman |
| 4,054,522 A | 10/1977 | Pinkerton |
| 4,060,485 A | 11/1977 | Eaton |
| 4,061,031 A | 12/1977 | Grimsrud |
| 4,067,803 A | 1/1978 | Quentin |
| 4,078,562 A | 3/1978 | Friedman |
| 4,081,372 A | 3/1978 | Atkin et al. |
| 4,102,655 A | 7/1978 | Jeffrey et al. |
| 4,115,259 A | 9/1978 | Bigi |
| 4,118,314 A | 10/1978 | Yoshida |
| 4,137,160 A | 1/1979 | Ebing et al. |
| 4,144,496 A | 3/1979 | Cunningham et al. |
| 4,149,860 A | 4/1979 | Kulik |
| 4,151,088 A | 4/1979 | Wolf, Jr. et al. |
| 4,151,407 A | 4/1979 | McBride et al. |
| 4,156,867 A | 5/1979 | Bench et al. |
| 4,164,320 A | 8/1979 | Irazoqui et al. |
| 4,173,537 A | 11/1979 | Newhart et al. |
| 4,173,971 A | 11/1979 | Karz |
| 4,180,460 A | 12/1979 | Calari |
| 4,181,245 A | 1/1980 | Garrett et al. |
| 4,190,047 A | 2/1980 | Jacobsen et al. |
| 4,191,182 A | 3/1980 | Popovich et al. |
| 4,191,646 A | 3/1980 | Larsson et al. |
| 4,192,748 A | 3/1980 | Hyden |
| 4,194,536 A | 3/1980 | Stine et al. |
| 4,199,307 A | 4/1980 | Jassawalla |
| 4,200,095 A | 4/1980 | Reti |
| 4,209,402 A | 6/1980 | Gentles |
| 4,212,738 A | 7/1980 | Henne |
| 4,213,859 A | 7/1980 | Smakman et al. |
| 4,229,299 A | 10/1980 | Savitz et al. |
| 4,240,408 A | 12/1980 | Schael |
| 4,244,816 A | 1/1981 | Vogler et al. |
| 4,247,393 A | 1/1981 | Wallace |
| 4,256,718 A | 3/1981 | McArthur et al. |
| 4,267,040 A | 5/1981 | Schal |
| 4,267,047 A | 5/1981 | Henne et al. |
| 4,269,708 A | 5/1981 | Bounomini et al. |
| 4,270,532 A | 6/1981 | Franetzki et al. |
| 4,273,121 A | 6/1981 | Jassawalla |
| 4,276,175 A | 6/1981 | Bower |
| 4,282,872 A | 8/1981 | Franetzki et al. |
| 4,293,413 A | 10/1981 | Schnell |
| 4,293,762 A | 10/1981 | Ogawa |
| 4,303,376 A | 12/1981 | Siekmann |
| 4,303,521 A | 12/1981 | Lehmann |
| 4,304,670 A | 12/1981 | Watanabe et al. |
| 4,308,866 A | 1/1982 | Jelliffe et al. |
| 4,311,137 A | 1/1982 | Gerard |
| 4,313,831 A | 2/1982 | Lehmann et al. |
| 4,319,338 A | 3/1982 | Grudowski et al. |
| 4,320,757 A | 3/1982 | Whitney et al. |
| 4,325,715 A | 4/1982 | Bowman et al. |
| 4,332,264 A | 6/1982 | Gortz |
| 4,338,190 A | 7/1982 | Kraus et al. |
| 4,344,777 A | 8/1982 | Siposs |
| 4,345,919 A | 8/1982 | Wilkinson et al. |
| 4,345,999 A | 8/1982 | Sigdell et al. |
| 4,348,280 A | 9/1982 | George et al. |
| 4,353,368 A | 10/1982 | Slovak et al. |
| 4,354,252 A | 10/1982 | Lamb et al. |

(56) References Cited

U.S. PATENT DOCUMENTS

| | | |
|---|---|---|
| 4,360,323 A | 11/1982 | Anderson |
| 4,360,507 A | 11/1982 | McArthur et al. |
| 4,363,641 A | 12/1982 | Finn, III |
| 4,364,747 A | 12/1982 | Blackshear et al. |
| 4,368,118 A | 1/1983 | Siposs |
| 4,369,780 A | 1/1983 | Sakai |
| 4,370,983 A | 2/1983 | Lichtenstein |
| 4,373,527 A | 2/1983 | Fischell |
| 4,381,003 A | 4/1983 | Buoncristiani |
| 4,381,776 A | 5/1983 | Latham, Jr. |
| 4,385,630 A | 5/1983 | Gilcher et al. |
| 4,386,634 A | 6/1983 | Stasz et al. |
| 4,398,289 A | 8/1983 | Schoate |
| 4,398,908 A | 8/1983 | Siposs |
| 4,416,654 A | 11/1983 | Schoendorfer et al. |
| 4,425,114 A | 1/1984 | Schoendorfer et al. |
| 4,427,009 A | 1/1984 | Wells et al. |
| 4,428,381 A | 1/1984 | Hepp |
| 4,433,971 A | 2/1984 | Lindsay et al. |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,460,555 A | 7/1984 | Thompson |
| 4,464,172 A | 8/1984 | Lichtenstein |
| 4,464,563 A | 8/1984 | Jewett |
| 4,469,481 A | 9/1984 | Kobayashi |
| 4,473,449 A | 9/1984 | Michaels et al. |
| 4,475,901 A | 10/1984 | Kraegen et al. |
| 4,476,381 A | 10/1984 | Rubin |
| 4,477,342 A | 10/1984 | Allan et al. |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,493,705 A | 1/1985 | Gordon et al. |
| 4,496,351 A | 1/1985 | Hillel et al. |
| 4,498,900 A | 2/1985 | Bouncristiani |
| 4,511,352 A | 4/1985 | Theeuwes et al. |
| 4,512,163 A | 4/1985 | Wells et al. |
| 4,525,861 A | 6/1985 | Freeburg |
| 4,529,401 A | 7/1985 | Leslie et al. |
| 4,531,527 A | 7/1985 | Reinhold, Jr. et al. |
| 4,531,937 A | 7/1985 | Yates |
| 4,532,414 A | 7/1985 | Shah et al. |
| 4,538,138 A | 8/1985 | Harvey et al. |
| 4,542,015 A | 9/1985 | Smakman et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,568,333 A | 2/1986 | Sawyer et al. |
| 4,581,141 A | 4/1986 | Ash |
| 4,583,981 A | 4/1986 | Urquhart et al. |
| 4,586,920 A | 5/1986 | Peabody |
| 4,586,925 A | 5/1986 | Carlsson et al. |
| 4,590,473 A | 5/1986 | Burke et al. |
| 4,602,249 A | 7/1986 | Abbott |
| 4,618,343 A | 10/1986 | Polaschegg |
| 4,619,653 A | 10/1986 | Fischell |
| 4,622,032 A | 11/1986 | Katsura et al. |
| 4,622,979 A | 11/1986 | Katchis et al. |
| 4,624,661 A | 11/1986 | Arimond |
| RE32,303 E | 12/1986 | Lasker et al. |
| 4,636,950 A | 1/1987 | Caswell et al. |
| 4,637,817 A | 1/1987 | Archibald et al. |
| 4,643,713 A | 2/1987 | Viitala |
| 4,643,715 A | 2/1987 | Isono et al. |
| 4,650,458 A | 3/1987 | Dahlberg et al. |
| 4,650,464 A | 3/1987 | Ruiz et al. |
| 4,650,469 A | 3/1987 | Berg et al. |
| 4,650,857 A | 3/1987 | May |
| 4,652,262 A | 3/1987 | Veracchi |
| 4,655,941 A | 4/1987 | Suzuki |
| 4,657,490 A | 4/1987 | Abbott |
| 4,661,246 A | 4/1987 | Ash |
| 4,664,891 A | 5/1987 | Cosentino et al. |
| 4,666,598 A | 5/1987 | Heath et al. |
| 4,670,007 A | 6/1987 | Wheeldon et al. |
| 4,676,776 A | 6/1987 | Howson |
| 4,678,460 A | 7/1987 | Rosner |
| 4,680,445 A | 7/1987 | Ogawa |
| 4,681,563 A | 7/1987 | Deckert et al. |
| 4,681,606 A | 7/1987 | Swan, Jr. et al. |
| 4,684,460 A | 8/1987 | Issautier |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,702,829 A | 10/1987 | Polaschegg et al. |
| 4,703,913 A | 11/1987 | Hunkapiller |
| 4,705,506 A | 11/1987 | Archibald |
| 4,708,802 A | 11/1987 | Rath et al. |
| 4,714,462 A | 12/1987 | DiComenico |
| 4,717,042 A | 1/1988 | McLaughlin |
| 4,718,576 A | 1/1988 | Tamura et al. |
| 4,718,890 A | 1/1988 | Peabody |
| 4,722,224 A | 2/1988 | Scheller et al. |
| 4,722,349 A | 2/1988 | Baumberg |
| 4,722,725 A | 2/1988 | Sawyer et al. |
| 4,722,731 A | 2/1988 | Vailancourt |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,734,198 A | 3/1988 | Harm et al. |
| 4,734,269 A | 3/1988 | Clarke et al. |
| 4,735,609 A | 4/1988 | Comeau et al. |
| 4,741,732 A | 5/1988 | Crankshaw et al. |
| 4,741,736 A | 5/1988 | Brown |
| 4,747,822 A | 5/1988 | Peabody |
| 4,756,706 A | 7/1988 | Kerns et al. |
| 4,759,756 A | 7/1988 | Forman |
| 4,765,907 A | 8/1988 | Scott |
| 4,767,399 A | 8/1988 | Bollish |
| 4,769,151 A | 9/1988 | Shouldice |
| 4,778,449 A | 10/1988 | Weber et al. |
| 4,778,451 A | 10/1988 | Kamen |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,804,474 A | 2/1989 | Blum |
| 4,806,135 A | 2/1989 | Siposs |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,543 A | 5/1989 | Weiss et al. |
| 4,828,545 A | 5/1989 | Epstein et al. |
| 4,830,018 A | 5/1989 | Treach |
| 4,831,562 A | 5/1989 | McIntosh et al. |
| 4,832,033 A | 5/1989 | Maher et al. |
| 4,835,372 A | 5/1989 | Beard et al. |
| 4,835,521 A | 5/1989 | Andrejasich et al. |
| 4,838,275 A | 6/1989 | Lee |
| 4,838,865 A | 6/1989 | Flank et al. |
| 4,839,806 A | 6/1989 | Goldfischer et al. |
| 4,844,074 A | 7/1989 | Kurucz |
| 4,845,644 A | 7/1989 | Anthias et al. |
| 4,847,470 A | 7/1989 | Bakke |
| 4,847,764 A | 7/1989 | Halvorson |
| 4,850,009 A | 7/1989 | Zook et al. |

(56) References Cited

U.S. PATENT DOCUMENTS

| | | |
|---|---|---|
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,576 A | 2/1990 | Philip |
| 4,898,578 A | 2/1990 | Rubalcaba, Jr. |
| 4,901,728 A | 2/1990 | Hutchison |
| 4,906,816 A | 3/1990 | van Leerdam |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,923,612 A | 5/1990 | Trivett et al. |
| 4,925,444 A | 5/1990 | Orkin et al. |
| 4,932,987 A | 6/1990 | Molina |
| 4,933,843 A | 6/1990 | Scheller et al. |
| 4,937,777 A | 6/1990 | Flood et al. |
| 4,941,808 A | 7/1990 | Qureshi et al. |
| 4,941,875 A | 7/1990 | Brennan |
| 4,943,279 A | 7/1990 | Samiotes et al. |
| 4,946,439 A | 8/1990 | Eggers |
| 4,949,274 A | 8/1990 | Hollander et al. |
| 4,950,259 A | 8/1990 | Geary et al. |
| 4,952,928 A | 8/1990 | Carroll et al. |
| 4,953,074 A | 8/1990 | Kametani et al. |
| 4,955,508 A | 9/1990 | Capanna et al. |
| D311,061 S | 10/1990 | Vrana et al. |
| 4,960,230 A | 10/1990 | Marelli |
| 4,966,579 A | 10/1990 | Polaschegg |
| 4,967,928 A | 11/1990 | Carter |
| 4,968,295 A | 11/1990 | Neumann |
| 4,976,683 A | 12/1990 | Gauthier et al. |
| 4,976,685 A | 12/1990 | Block, Jr. |
| 4,977,590 A | 12/1990 | Milovancevic |
| 4,978,335 A | 12/1990 | Arthur |
| 4,991,091 A | 2/1991 | Allen |
| 4,992,926 A | 2/1991 | Janke et al. |
| 4,993,068 A | 2/1991 | Piosenka et al. |
| 4,997,464 A | 3/1991 | Kopf |
| 4,998,249 A | 3/1991 | Bennett et al. |
| 5,002,055 A | 3/1991 | Merki et al. |
| 5,002,471 A | 3/1991 | Perlov |
| 5,003,296 A | 3/1991 | Lee |
| 5,004,459 A | 4/1991 | Peabody et al. |
| 5,006,699 A | 4/1991 | Felkner et al. |
| 5,007,429 A | 4/1991 | Treatch et al. |
| 5,011,607 A | 4/1991 | Shinzato |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,032,265 A | 7/1991 | Jha et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,147 A | 9/1991 | Chevallet et al. |
| 5,047,959 A | 9/1991 | Phillips et al. |
| 5,049,492 A | 9/1991 | Sauer et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,059,173 A | 10/1991 | Sacco |
| 5,061,236 A | 10/1991 | Sutherland et al. |
| 5,061,243 A | 10/1991 | Winchell et al. |
| 5,061,365 A | 10/1991 | Utterberg |
| 5,062,774 A | 11/1991 | Kramer et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,073,167 A | 12/1991 | Carr et al. |
| 5,078,683 A | 1/1992 | Sancoff et al. |
| 5,084,828 A | 1/1992 | Kaufman et al. |
| 5,087,245 A | 2/1992 | Doan |
| 5,088,515 A | 2/1992 | Kamen |
| 5,088,904 A | 2/1992 | Okada |
| 5,088,981 A | 2/1992 | Howson et al. |
| 5,088,990 A | 2/1992 | Hivale et al. |
| 5,091,094 A | 2/1992 | Veech |
| 5,096,385 A | 3/1992 | Georgi et al. |
| 5,098,377 A | 3/1992 | Borsanyi et al. |
| 5,100,380 A | 3/1992 | Adaniya et al. |
| 5,104,374 A | 4/1992 | Bishko et al. |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,112,480 A | 5/1992 | Hukasawa |
| 5,114,580 A | 5/1992 | Ahmad et al. |
| 5,116,203 A | 5/1992 | Natwick et al. |
| 5,116,312 A | 5/1992 | Blankenship et al. |
| 5,120,303 A | 6/1992 | Hombrouckx |
| 5,122,516 A | 6/1992 | Watanabe et al. |
| 5,125,069 A | 6/1992 | O'Boyle |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,141,492 A | 8/1992 | Dadson et al. |
| 5,141,493 A | 8/1992 | Jacobson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,167,921 A | 12/1992 | Gordon |
| 5,172,698 A | 12/1992 | Stanko |
| 5,173,125 A | 12/1992 | Felding |
| 5,176,004 A | 1/1993 | Gaudet |
| 5,178,763 A | 1/1993 | Delaunay |
| 5,179,569 A | 1/1993 | Sawyer |
| 5,179,700 A | 1/1993 | Aihara et al. |
| 5,180,896 A | 1/1993 | Gibby et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,204,000 A | 4/1993 | Steadman et al. |
| 5,208,907 A | 5/1993 | Shelton et al. |
| 5,211,849 A | 5/1993 | Benzing et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,221,267 A | 6/1993 | Folden |
| 5,225,974 A | 7/1993 | Mathews et al. |
| 5,226,425 A | 7/1993 | Righter |
| 5,228,450 A | 7/1993 | Sellers |
| 5,228,889 A | 7/1993 | Cortial et al. |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,236,476 A | 8/1993 | Klick |

(56) References Cited

U.S. PATENT DOCUMENTS

| | | |
|---|---|---|
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,693 A | 9/1993 | Ford et al. |
| 5,245,704 A | 9/1993 | Weber et al. |
| 5,246,560 A | 9/1993 | Nekoksa et al. |
| 5,254,096 A | 10/1993 | Rondelet et al. |
| 5,256,156 A | 10/1993 | Kern et al. |
| 5,256,157 A | 10/1993 | Samiotes et al. |
| 5,256,371 A | 10/1993 | Pippert |
| 5,259,954 A | 11/1993 | Taylor |
| 5,259,961 A | 11/1993 | Eigendorf |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,268,077 A | 12/1993 | Bubik et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,274,434 A | 12/1993 | Morioka et al. |
| 5,277,188 A | 1/1994 | Selker |
| 5,277,820 A | 1/1994 | Ash |
| 5,283,861 A | 2/1994 | Dangler et al. |
| 5,284,150 A | 2/1994 | Butterfield et al. |
| 5,284,470 A | 2/1994 | Beltz |
| 5,286,252 A | 2/1994 | Tuttle et al. |
| 5,292,029 A | 3/1994 | Pearson |
| 5,295,505 A | 3/1994 | Polaschegg et al. |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,318,750 A | 6/1994 | Lascombes |
| 5,319,543 A | 6/1994 | Wilhelm |
| 5,321,618 A | 6/1994 | Gessman |
| 5,321,829 A | 6/1994 | Zifferer |
| 5,325,478 A | 6/1994 | Shelton et al. |
| 5,326,473 A | 7/1994 | Lascombes et al. |
| 5,327,341 A | 7/1994 | Whalen et al. |
| 5,330,420 A | 7/1994 | Lee |
| 5,331,549 A | 7/1994 | Crawford, Jr. |
| 5,336,165 A | 8/1994 | Twardowski |
| 5,336,173 A | 8/1994 | Folden |
| 5,336,245 A | 8/1994 | Adams et al. |
| 5,337,230 A | 8/1994 | Baumgartner et al. |
| 5,338,157 A | 8/1994 | Blomquist |
| 5,338,293 A | 8/1994 | Jeppsson et al. |
| 5,339,821 A | 8/1994 | Fujimoto |
| 5,341,291 A | 8/1994 | Roizen et al. |
| 5,341,412 A | 8/1994 | Ramot et al. |
| D350,822 S | 9/1994 | Lanigan |
| D350,823 S | 9/1994 | Lanigan |
| 5,348,008 A | 9/1994 | Bornn et al. |
| 5,348,539 A | 9/1994 | Herskowitz |
| 5,349,675 A | 9/1994 | Fitzgerald et al. |
| 5,350,357 A | 9/1994 | Kamen et al. |
| 5,356,376 A | 10/1994 | Milijasevic et al. |
| 5,356,378 A | 10/1994 | Doan |
| 5,358,481 A | 10/1994 | Todd et al. |
| 5,361,202 A | 11/1994 | Doue |
| 5,361,758 A | 11/1994 | Hall et al. |
| 5,366,630 A | 11/1994 | Chevallet |
| 5,366,896 A | 11/1994 | Margrey et al. |
| 5,366,904 A | 11/1994 | Qureshi et al. |
| 5,367,555 A | 11/1994 | Isoyama |
| 5,368,555 A | 11/1994 | Sussman et al. |
| 5,368,562 A | 11/1994 | Blomquist et al. |
| 5,370,612 A | 12/1994 | Maeda et al. |
| 5,370,674 A | 12/1994 | Farrell |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Colman et al. |
| 5,376,263 A | 12/1994 | Fischel |
| 5,377,864 A | 1/1995 | Blechl et al. |
| 5,378,231 A | 1/1995 | Johnson et al. |
| 5,379,214 A | 1/1995 | Arbuckle et al. |
| 5,381,510 A | 1/1995 | Ford et al. |
| 5,385,564 A | 1/1995 | Slater et al. |
| 5,389,078 A | 2/1995 | Zalesky et al. |
| 5,390,238 A | 2/1995 | Kirk et al. |
| 5,392,951 A | 2/1995 | Gardner et al. |
| 5,394,732 A | 3/1995 | Johnson et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,401,342 A | 3/1995 | Vincent et al. |
| D357,312 S | 4/1995 | Riquier et al. |
| 5,404,292 A | 4/1995 | Hendrickson |
| 5,404,384 A | 4/1995 | Colburn et al. |
| 5,406,473 A | 4/1995 | Yoshikura et al. |
| 5,408,576 A | 4/1995 | Bishop |
| 5,411,472 A | 5/1995 | Steg, Jr. et al. |
| 5,411,705 A | 5/1995 | Thor et al. |
| 5,412,715 A | 5/1995 | Volpe |
| 5,415,167 A | 5/1995 | Wilk |
| 5,416,695 A | 5/1995 | Miller et al. |
| 5,417,222 A | 5/1995 | Dempsey et al. |
| 5,420,962 A | 5/1995 | Bakke |
| 5,420,977 A | 5/1995 | Sztipanovits et al. |
| 5,421,343 A | 6/1995 | Feng |
| 5,421,815 A | 6/1995 | Noguchi et al. |
| 5,423,746 A | 6/1995 | Burkett et al. |
| 5,429,595 A | 7/1995 | Wright, Jr. et al. |
| 5,429,602 A | 7/1995 | Hauser |
| 5,431,299 A | 7/1995 | Brewer et al. |
| 5,431,627 A | 7/1995 | Pastrone et al. |
| 5,433,736 A | 7/1995 | Nilsson |
| 5,438,510 A | 8/1995 | Bryant et al. |
| 5,438,607 A | 8/1995 | Przygoda, Jr. et al. |
| 5,440,699 A | 8/1995 | Farrand et al. |
| 5,441,047 A | 8/1995 | David et al. |
| 5,441,636 A | 8/1995 | Chevallet et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,468,388 A | 11/1995 | Goddard et al. |
| 5,469,855 A | 11/1995 | Pompei et al. |
| 5,470,483 A | 11/1995 | Bene et al. |
| 5,471,382 A | 11/1995 | Tallman et al. |
| 5,474,552 A | 12/1995 | Palti |
| 5,474,683 A | 12/1995 | Bryant et al. |
| 5,482,043 A | 1/1996 | Zulauf |
| 5,482,446 A | 1/1996 | Williamson et al. |
| 5,484,397 A | 1/1996 | Twardowski |
| 5,485,408 A | 1/1996 | Blomquist |
| 5,489,385 A | 2/1996 | Raabe et al. |
| 5,490,610 A | 2/1996 | Pearson |
| 5,490,925 A | 2/1996 | Eigendorf |
| 5,494,592 A | 2/1996 | Latham, Jr. et al. |
| 5,496,265 A | 3/1996 | Langley et al. |
| 5,496,273 A | 3/1996 | Pastrone et al. |
| 5,498,338 A | 3/1996 | Kruger et al. |

(56) References Cited

U.S. PATENT DOCUMENTS

| | | |
|---|---|---|
| 5,502,944 A | 4/1996 | Kraft et al. |
| 5,503,801 A | 4/1996 | Brugger |
| 5,507,412 A | 4/1996 | Ebert et al. |
| 5,508,912 A | 4/1996 | Schneiderman |
| 5,509,422 A | 4/1996 | Fukami |
| 5,509,895 A | 4/1996 | Noguchi et al. |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,520,640 A | 5/1996 | Utterberg |
| 5,522,396 A | 6/1996 | Langer et al. |
| 5,522,798 A | 6/1996 | Johnson et al. |
| 5,522,998 A | 6/1996 | Polaschegg |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,540,808 A | 7/1996 | Vincent et al. |
| 5,540,842 A | 7/1996 | Aoyama et al. |
| 5,542,420 A | 8/1996 | Goldman et al. |
| 5,542,919 A | 8/1996 | Simon et al. |
| 5,544,649 A | 8/1996 | David et al. |
| 5,544,651 A | 8/1996 | Wilk |
| 5,544,661 A | 8/1996 | Davis et al. |
| 5,545,131 A | 8/1996 | Davankov |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,570,026 A | 10/1996 | Buffaloe, IV et al. |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,578,070 A | 11/1996 | Utterberg |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | McIlroy et al. |
| 5,588,815 A | 12/1996 | Zaleski, II |
| 5,588,816 A | 12/1996 | Abbott et al. |
| 5,589,932 A | 12/1996 | Garcia-Rubio et al. |
| 5,590,648 A | 1/1997 | Mitchell et al. |
| 5,591,251 A | 1/1997 | Brugger |
| 5,591,344 A | 1/1997 | Kenley et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,605,540 A | 2/1997 | Utterberg |
| 5,609,572 A | 3/1997 | Lang |
| 5,609,575 A | 3/1997 | Larson et al. |
| 5,609,576 A | 3/1997 | Voss et al. |
| 5,613,115 A | 3/1997 | Gihl et al. |
| 5,614,677 A | 3/1997 | Wansiedler et al. |
| 5,616,248 A | 4/1997 | Schal |
| 5,619,428 A | 4/1997 | Lee et al. |
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,628,908 A | 5/1997 | Kamen |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,081 A | 6/1997 | Noguchi et al. |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,640,995 A | 6/1997 | Packard et al. |
| 5,641,405 A | 6/1997 | Keshaviah et al. |
| 5,641,628 A | 6/1997 | Bianchi |
| 5,643,193 A | 7/1997 | Papillon et al. |
| 5,643,201 A | 7/1997 | Peabody et al. |
| 5,643,212 A | 7/1997 | Coutre et al. |
| 5,643,250 A | 7/1997 | Utterberg |
| 5,645,734 A | 7/1997 | Kenley et al. |
| 5,647,853 A | 7/1997 | Feldmann et al. |
| 5,647,854 A | 7/1997 | Olsen et al. |
| 5,650,071 A | 7/1997 | Brugger et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,658,456 A | 8/1997 | Kenley et al. |
| 5,661,978 A | 9/1997 | Holmes et al. |
| 5,664,270 A | 9/1997 | Bell et al. |
| 5,666,404 A | 9/1997 | Ciccotelli et al. |
| 5,674,199 A | 10/1997 | Brugger |
| 5,678,562 A | 10/1997 | Sellers |
| 5,678,568 A | 10/1997 | Uchikubo et al. |
| 5,681,285 A | 10/1997 | Ford et al. |
| 5,681,294 A | 10/1997 | Osborne et al. |
| 5,682,526 A | 10/1997 | Smokoff et al. |
| 5,683,355 A | 11/1997 | Fini et al. |
| 5,683,367 A | 11/1997 | Jordan et al. |
| 5,683,381 A | 11/1997 | Carr et al. |
| 5,685,844 A | 11/1997 | Marttila |
| 5,685,988 A | 11/1997 | Malchesky |
| 5,685,989 A | 11/1997 | Krivitski et al. |
| 5,687,717 A | 11/1997 | Halpern |
| 5,687,734 A | 11/1997 | Dempsey et al. |
| 5,690,614 A | 11/1997 | Carr et al. |
| 5,690,831 A | 11/1997 | Kenley et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,702,597 A | 12/1997 | Chevallet et al. |
| 5,702,606 A | 12/1997 | Peter, Jr. et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |

(56) References Cited

U.S. PATENT DOCUMENTS

| | | |
|---|---|---|
| RE35,743 E | 3/1998 | Pearson |
| 5,722,947 A | 3/1998 | Jeppsson et al. |
| 5,724,025 A | 3/1998 | Tavori |
| 5,724,478 A | 3/1998 | Thweatt |
| 5,724,580 A | 3/1998 | Levin et al. |
| 5,725,776 A | 3/1998 | Kenley et al. |
| 5,729,653 A | 3/1998 | Magliochetti et al. |
| 5,730,712 A | 3/1998 | Falkvall et al. |
| 5,730,730 A | 3/1998 | Darling, Jr. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,744,042 A | 4/1998 | Stange et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,762,782 A | 6/1998 | Kenley et al. |
| 5,763,266 A | 6/1998 | Palsson et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur |
| 5,772,637 A | 6/1998 | Heinzmann et al. |
| 5,776,057 A | 7/1998 | Swenson et al. |
| 5,776,091 A | 7/1998 | Brugger et al. |
| 5,776,345 A | 7/1998 | Truitt et al. |
| 5,778,345 A | 7/1998 | McCartney |
| 5,778,882 A | 7/1998 | Raymond et al. |
| 5,781,442 A | 7/1998 | Chamberlain et al. |
| 5,782,575 A | 7/1998 | Vincent et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,790,409 A | 8/1998 | Fedor et al. |
| 5,790,752 A | 8/1998 | Anglin et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,803,906 A | 9/1998 | Pratt et al. |
| 5,805,442 A | 9/1998 | Crater et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Chen et al. |
| 5,810,747 A | 9/1998 | Brudny et al. |
| 5,814,015 A | 9/1998 | Cowen et al. |
| 5,815,566 A | 9/1998 | Ramot et al. |
| 5,816,779 A | 10/1998 | Lawless et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,830,185 A | 11/1998 | Block, Jr. |
| 5,832,448 A | 11/1998 | Brown |
| 5,832,450 A | 11/1998 | Myers et al. |
| 5,833,599 A | 11/1998 | Schrier et al. |
| 5,836,908 A | 11/1998 | Beden et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,846,419 A | 12/1998 | Nederlof |
| 5,848,593 A | 12/1998 | McGrady et al. |
| 5,849,065 A | 12/1998 | Wojke |
| 5,851,186 A | 12/1998 | Wood et al. |
| 5,851,202 A | 12/1998 | Carlsson |
| 5,852,590 A | 12/1998 | De La Huerga |
| 5,853,387 A | 12/1998 | Clegg et al. |
| 5,855,550 A | 1/1999 | Buyan et al. |
| 5,857,967 A | 1/1999 | Frid et al. |
| 5,858,238 A | 1/1999 | McRea et al. |
| 5,858,239 A | 1/1999 | Kenley et al. |
| 5,859,972 A | 1/1999 | Subramaniam et al. |
| 5,863,421 A | 1/1999 | Peter, Jr. et al. |
| 5,865,745 A | 2/1999 | Schmitt et al. |
| 5,865,786 A | 2/1999 | Sibalis et al. |
| 5,866,880 A | 2/1999 | Seitz et al. |
| 5,867,821 A | 2/1999 | Ballantyne et al. |
| 5,871,465 A | 2/1999 | Vasko |
| 5,871,694 A | 2/1999 | Beden et al. |
| 5,873,853 A | 2/1999 | Keilman et al. |
| 5,875,282 A | 2/1999 | Jordan et al. |
| 5,876,611 A | 3/1999 | Shettigar |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zini et al. |
| 5,894,273 A | 4/1999 | Meador et al. |
| 5,895,368 A | 4/1999 | Utterberg |
| 5,895,371 A | 4/1999 | Jordan et al. |
| 5,895,578 A | 4/1999 | Simard et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Dupouy et al. |
| 5,902,336 A | 5/1999 | Mishkin |
| 5,902,476 A | 5/1999 | Twardowski |
| 5,904,668 A | 5/1999 | Hyman et al. |
| 5,905,653 A | 5/1999 | Higham et al. |
| 5,907,291 A | 5/1999 | Chen et al. |
| 5,908,027 A | 6/1999 | Butterfield et al. |
| 5,910,107 A | 6/1999 | Iliff |
| 5,910,252 A | 6/1999 | Corbin, III et al. |
| 5,911,132 A | 6/1999 | Sloane |
| 5,911,687 A | 6/1999 | Sano et al. |
| 5,912,818 A | 6/1999 | McGrady et al. |
| 5,913,197 A | 6/1999 | Kameda |
| 5,913,310 A | 6/1999 | Brown |
| 5,915,240 A | 6/1999 | Karpf |
| 5,919,154 A | 7/1999 | Toavs et al. |
| 5,919,369 A | 7/1999 | Ash |
| 5,921,938 A | 7/1999 | Aoyama et al. |
| 5,921,951 A | 7/1999 | Morris |
| 5,923,018 A | 7/1999 | Kameda et al. |
| 5,924,074 A | 7/1999 | Evans |
| 5,924,103 A | 7/1999 | Ahmed et al. |
| 5,925,011 A | 7/1999 | Faict et al. |
| 5,927,540 A | 7/1999 | Godlewski |
| 5,928,744 A | 7/1999 | Heilmann et al. |
| 5,928,889 A | 7/1999 | Bakich et al. |
| 5,931,791 A | 8/1999 | Saltzstein et al. |
| 5,931,990 A | 8/1999 | Andrews |
| 5,932,103 A | 8/1999 | Kenley et al. |
| 5,932,110 A | 8/1999 | Shah |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,938,634 A | 8/1999 | Packard |
| 5,939,326 A | 8/1999 | Chupp et al. |
| 5,939,699 A | 8/1999 | Perttunen et al. |

(56) References Cited

U.S. PATENT DOCUMENTS

| | | |
|---|---|---|
| 5,940,306 A | 8/1999 | Gardner et al. |
| 5,940,802 A | 8/1999 | Hildebrand et al. |
| 5,941,829 A | 8/1999 | Saltzstein et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,944,684 A | 8/1999 | Roberts et al. |
| 5,945,651 A | 8/1999 | Chorosinski et al. |
| 5,946,083 A | 8/1999 | Melendez et al. |
| 5,946,659 A | 8/1999 | Lancelot et al. |
| 5,948,251 A | 9/1999 | Brugger |
| 5,950,006 A | 9/1999 | Crater et al. |
| 5,951,300 A | 9/1999 | Brown |
| 5,951,510 A | 9/1999 | Barak |
| 5,951,870 A | 9/1999 | Utterberg |
| 5,954,640 A | 9/1999 | Szabo |
| 5,954,885 A | 9/1999 | Bollish et al. |
| 5,954,958 A | 9/1999 | Folden |
| 5,954,971 A | 9/1999 | Pages et al. |
| 5,956,023 A | 9/1999 | Lyle et al. |
| 5,957,153 A | 9/1999 | Frey et al. |
| 5,957,885 A | 9/1999 | Bollish et al. |
| 5,959,529 A | 9/1999 | Kail, IV |
| 5,960,085 A | 9/1999 | De La Huerga |
| 5,960,160 A | 9/1999 | Clark et al. |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,481 A | 11/1999 | Gorsuch |
| 5,980,490 A | 11/1999 | Tsoukalis |
| 5,980,741 A | 11/1999 | Schnell et al. |
| 5,983,193 A | 11/1999 | Heinonen et al. |
| 5,983,947 A | 11/1999 | Utterberg |
| 5,984,891 A | 11/1999 | Keilman et al. |
| 5,987,519 A | 11/1999 | Peifer et al. |
| 5,989,238 A | 11/1999 | Ginsburg |
| 5,989,318 A | 11/1999 | Schroll |
| 5,989,423 A | 11/1999 | Kamen et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,965 A | 11/1999 | Experton |
| 5,997,167 A | 12/1999 | Crater et al. |
| 5,997,476 A | 12/1999 | Brown |
| 6,001,201 A | 12/1999 | Vincent et al. |
| 6,003,006 A | 12/1999 | Colella et al. |
| 6,004,020 A | 12/1999 | Bartur |
| 6,004,276 A | 12/1999 | Wright et al. |
| 6,004,311 A | 12/1999 | Heilmann et al. |
| 6,006,191 A | 12/1999 | DeRienzo |
| 6,009,333 A | 12/1999 | Chaco |
| 6,010,454 A | 1/2000 | Arieff et al. |
| 6,010,623 A | 1/2000 | Schnell et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,019,824 A | 2/2000 | Schnell |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Allen et al. |
| 6,024,720 A | 2/2000 | Chandler et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Crone et al. |
| 6,039,467 A | 3/2000 | Holmes |
| 6,042,784 A | 3/2000 | Wamsiedler et al. |
| 6,046,806 A | 4/2000 | Thompson |
| 6,047,259 A | 4/2000 | Campbell et al. |
| 6,050,940 A | 4/2000 | Braun et al. |
| 6,051,134 A | 4/2000 | Schnell et al. |
| 6,053,967 A | 4/2000 | Heilmann et al. |
| 6,055,487 A | 4/2000 | Margery |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,066,111 A | 5/2000 | Brockhoff |
| 6,068,153 A | 5/2000 | Young et al. |
| 6,069,343 A | 5/2000 | Kolowich |
| 6,071,269 A | 6/2000 | Schnell et al. |
| 6,073,046 A | 6/2000 | Patel et al. |
| 6,074,345 A | 6/2000 | van Oostrom et al. |
| 6,074,359 A | 6/2000 | Keshaviah et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,342 A | 9/2000 | Schnell et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,129,699 A | 10/2000 | Haight et al. |
| 6,132,371 A | 10/2000 | Dempsey et al. |
| 6,132,616 A | 10/2000 | Twardowski et al. |
| 6,134,504 A | 10/2000 | Douglas et al. |
| 6,135,949 A | 10/2000 | Russo et al. |
| 6,139,495 A | 10/2000 | De La Huerga |
| 6,139,528 A | 10/2000 | Kistner et al. |
| 6,139,748 A | 10/2000 | Ericson et al. |
| 6,139,754 A | 10/2000 | Hartranft |
| 6,139,757 A | 10/2000 | Ohmura |
| 6,142,974 A | 11/2000 | Kistner et al. |
| 6,142,975 A | 11/2000 | Kistner et al. |
| 6,144,922 A | 11/2000 | Douglas et al. |
| 6,145,695 A | 11/2000 | Garrigues |
| 6,146,359 A | 11/2000 | Carr et al. |
| 6,146,523 A | 11/2000 | Barrett et al. |
| 6,146,536 A | 11/2000 | Twardowski |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |

(56) References Cited

U.S. PATENT DOCUMENTS

| | | | |
|---|---|---|---|
| 6,160,478 | A | 12/2000 | Jacobsen et al. |
| 6,161,095 | A | 12/2000 | Brown |
| 6,163,737 | A | 12/2000 | Fedor et al. |
| 6,165,154 | A | 12/2000 | Gray et al. |
| 6,168,563 | B1 | 1/2001 | Brown |
| 6,168,578 | B1 | 1/2001 | Diamond |
| 6,170,007 | B1 | 1/2001 | Venkatraman et al. |
| 6,170,746 | B1 | 1/2001 | Brook et al. |
| 6,171,112 | B1 | 1/2001 | Clark et al. |
| 6,171,237 | B1 | 1/2001 | Boaz et al. |
| 6,171,264 | B1 | 1/2001 | Bader |
| 6,171,484 | B1 | 1/2001 | Schnell et al. |
| 6,173,198 | B1 | 1/2001 | Schulze et al. |
| 6,175,688 | B1 | 1/2001 | Cassidy et al. |
| 6,175,779 | B1 | 1/2001 | Barrett |
| 6,175,977 | B1 | 1/2001 | Schumacher et al. |
| 6,176,903 | B1 | 1/2001 | Wamsiedler |
| 6,182,047 | B1 | 1/2001 | Dirbas |
| 6,183,417 | B1 | 2/2001 | Geheb et al. |
| 6,186,145 | B1 | 2/2001 | Brown |
| 6,187,198 | B1 | 2/2001 | Utterberg |
| 6,188,988 | B1 | 2/2001 | Barry et al. |
| 6,192,320 | B1 | 2/2001 | Margrey et al. |
| 6,193,480 | B1 | 2/2001 | Butterfield |
| 6,193,684 | B1 | 2/2001 | Burbank et al. |
| 6,195,887 | B1 | 3/2001 | Danby et al. |
| 6,196,992 | B1 | 3/2001 | Keilman et al. |
| 6,198,394 | B1 | 3/2001 | Jacobsen et al. |
| 6,200,264 | B1 | 3/2001 | Satherley et al. |
| 6,200,289 | B1 | 3/2001 | Hochman et al. |
| 6,203,495 | B1 | 3/2001 | Bardy |
| 6,203,528 | B1 | 3/2001 | Deckert et al. |
| 6,206,238 | B1 | 3/2001 | Ophardt |
| 6,206,829 | B1 | 3/2001 | Iliff |
| 6,206,954 | B1 | 3/2001 | Schnell et al. |
| 6,210,361 | B1 | 4/2001 | Kamen et al. |
| 6,213,391 | B1 | 4/2001 | Lewis |
| 6,213,738 | B1 | 4/2001 | Danby et al. |
| 6,219,439 | B1 | 4/2001 | Burger |
| 6,219,587 | B1 | 4/2001 | Ahlin et al. |
| 6,220,299 | B1 | 4/2001 | Arvidsson et al. |
| 6,221,011 | B1 | 4/2001 | Bardy |
| 6,221,012 | B1 | 4/2001 | Maschke et al. |
| 6,222,619 | B1 | 4/2001 | Herron et al. |
| 6,224,549 | B1 | 5/2001 | Van Drongelen |
| 6,225,901 | B1 | 5/2001 | Kail, IV |
| 6,226,564 | B1 | 5/2001 | Stuart |
| 6,228,047 | B1 | 5/2001 | Dadson |
| 6,229,957 | B1 | 5/2001 | Baker |
| 6,230,927 | B1 | 5/2001 | Schoonen et al. |
| 6,234,991 | B1 | 5/2001 | Gorsuch |
| 6,234,992 | B1 | 5/2001 | Haight et al. |
| 6,234,997 | B1 | 5/2001 | Kamen et al. |
| 6,236,809 | B1 | 5/2001 | Cassidy et al. |
| 6,245,013 | B1 | 6/2001 | Minoz et al. |
| 6,245,039 | B1 | 6/2001 | Brugger et al. |
| 6,246,473 | B1 | 6/2001 | Smith, Jr. et al. |
| 6,248,063 | B1 | 6/2001 | Barnhill et al. |
| 6,248,065 | B1 | 6/2001 | Brown |
| 6,251,167 | B1 | 6/2001 | Berson |
| 6,251,279 | B1 | 6/2001 | Peterson et al. |
| 6,254,567 | B1 | 7/2001 | Treu et al. |
| 6,255,951 | B1 | 7/2001 | De La Huerga |
| 6,256,643 | B1 | 7/2001 | Cork et al. |
| 6,256,967 | B1 | 7/2001 | Hebron et al. |
| 6,259,355 | B1 | 7/2001 | Chaco et al. |
| 6,259,654 | B1 | 7/2001 | De La Huerga |
| 6,260,715 | B1 | 7/2001 | Simard et al. |
| 6,261,261 | B1 | 7/2001 | Gordon |
| 6,261,809 | B1 | 7/2001 | Bertling et al. |
| 6,266,645 | B1 | 7/2001 | Simpson |
| 6,269,340 | B1 | 7/2001 | Ford et al. |
| D446,854 | S | 8/2001 | Cheney, II et al. |
| 6,270,455 | B1 | 8/2001 | Brown |
| 6,270,457 | B1 | 8/2001 | Bardy |
| 6,272,394 | B1 | 8/2001 | Lipps |
| 6,272,505 | B1 | 8/2001 | De La Huerga |
| 6,274,034 | B1 | 8/2001 | Nikaido et al. |
| 6,274,103 | B1 | 8/2001 | Taylor |
| 6,277,072 | B1 | 8/2001 | Bardy |
| 6,280,632 | B1 | 8/2001 | Polaschegg |
| 6,280,634 | B1 | 8/2001 | Shah et al. |
| 6,283,322 | B1 | 9/2001 | Liff et al. |
| 6,283,944 | B1 | 9/2001 | McMullen et al. |
| 6,287,516 | B1 | 9/2001 | Matson et al. |
| 6,290,646 | B1 | 9/2001 | Cosentino |
| 6,290,650 | B1 | 9/2001 | Butterfield et al. |
| 6,290,669 | B1 | 9/2001 | Zicherman |
| 6,293,921 | B1 | 9/2001 | Shinmoto et al. |
| 6,294,999 | B1 | 9/2001 | Yarin et al. |
| 6,295,506 | B1 | 9/2001 | Heinonen |
| 6,302,653 | B1 | 10/2001 | Bryant et al. |
| 6,304,788 | B1 | 10/2001 | Eady et al. |
| 6,306,088 | B1 | 10/2001 | Krausman et al. |
| 6,307,956 | B1 | 10/2001 | Black |
| 6,308,171 | B1 | 10/2001 | De La Huerga |
| 6,309,673 | B1 | 10/2001 | Duponchelle |
| 6,311,163 | B1 | 10/2001 | Sheehan et al. |
| 6,312,227 | B1 | 11/2001 | Davis |
| 6,312,378 | B1 | 11/2001 | Bardy |
| 6,312,414 | B1 | 11/2001 | Brockhoff et al. |
| 6,314,384 | B1 | 11/2001 | Goetz |
| 6,315,895 | B1 | 11/2001 | Summerton et al. |
| 6,317,719 | B1 | 11/2001 | Schrier et al. |
| 6,319,200 | B1 | 11/2001 | Lai |
| 6,319,221 | B1 | 11/2001 | Savage et al. |
| 6,321,203 | B1 | 11/2001 | Kameda |
| 6,322,504 | B1 | 11/2001 | Kirshner |
| 6,322,515 | B1 | 11/2001 | Goor et al. |
| 6,322,551 | B1 | 11/2001 | Brugger |
| 6,331,252 | B1 | 12/2001 | El Sayyid et al. |
| RE37,531 | E | 1/2002 | Chaco et al. |
| 6,337,631 | B1 | 1/2002 | Pai |
| 6,338,007 | B1 | 1/2002 | Broadfield et al. |
| 6,339,732 | B1 | 1/2002 | Phoon et al. |
| 6,344,139 | B1 | 2/2002 | Utterberg |
| 6,345,260 | B1 | 2/2002 | Cummings, Jr. et al. |
| 6,346,886 | B1 | 2/2002 | De La Huerga |
| 6,348,162 | B1 | 2/2002 | Ash |
| 6,352,200 | B1 | 3/2002 | Schoonen et al. |
| 6,353,817 | B1 | 3/2002 | Jacobs et al. |
| 6,357,600 | B1 | 3/2002 | Scagliarini |
| 6,358,225 | B1 | 3/2002 | Butterfield |
| 6,358,237 | B1 | 3/2002 | Paukovits |
| 6,361,201 | B1 | 3/2002 | Russell et al. |
| 6,361,263 | B1 | 3/2002 | Dewey et al. |
| 6,362,591 | B1 | 3/2002 | Moberg |
| 6,363,282 | B1 | 3/2002 | Nichols et al. |
| 6,363,290 | B1 | 3/2002 | Lyle et al. |
| 6,366,282 | B1 | 3/2002 | Nichols et al. |
| 6,364,143 | B1 | 4/2002 | Knierbein |
| 6,364,834 | B1 | 4/2002 | Reuss et al. |
| 6,364,857 | B1 | 4/2002 | Gray et al. |
| 6,368,273 | B1 | 4/2002 | Brown |
| 6,370,841 | B1 | 4/2002 | Chudy et al. |
| 6,381,577 | B1 | 4/2002 | Brown |
| 6,382,923 | B1 | 5/2002 | Gray |
| 6,385,505 | B1 | 5/2002 | Lipps |
| 6,391,541 | B1 | 5/2002 | Petersen et al. |
| 6,391,638 | B1 | 5/2002 | Shaaltiel |
| 6,393,369 | B1 | 5/2002 | Carr |
| 6,397,190 | B1 | 5/2002 | Goetz |
| 6,402,702 | B1 | 6/2002 | Gilcher et al. |
| 6,406,426 | B1 | 6/2002 | Reuss et al. |
| 6,406,631 | B1 | 6/2002 | Collins et al. |
| 6,407,335 | B1 | 6/2002 | Franklin-Lees et al. |
| 6,408,330 | B1 | 6/2002 | De La Huerga |
| 6,416,293 | B1 | 7/2002 | Bouchard et al. |
| 6,416,471 | B1 | 7/2002 | Kumar et al. |
| 6,421,650 | B1 | 7/2002 | Goetz et al. |
| 6,426,056 | B2 | 7/2002 | Taylor |
| 6,427,088 | B1 | 7/2002 | Bowman, IV et al. |
| 6,434,531 | B1 | 8/2002 | Lancelot et al. |
| 6,434,569 | B1 | 8/2002 | Tomlinson et al. |

(56) References Cited

U.S. PATENT DOCUMENTS

| | | |
|---|---|---|
| 6,449,927 B2 | 9/2002 | Hebron et al. |
| 6,450,956 B1 | 9/2002 | Rappaport et al. |
| 6,458,102 B1 | 10/2002 | Mann et al. |
| 6,464,977 B2 | 10/2002 | Kai et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,489,301 B1 | 12/2002 | Kobira et al. |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,579,253 B1 | 6/2003 | Burbank et al. |
| 6,581,069 B1 | 6/2003 | Robinson et al. |
| 6,582,385 B2 | 6/2003 | Burbank et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,595,944 B2 | 7/2003 | Balschat et al. |
| 6,602,502 B1 | 8/2003 | Strahilevitz |
| 6,607,485 B2 | 8/2003 | Bardy |
| 6,613,009 B1 | 9/2003 | Bainbridge et al. |
| 6,623,709 B2 | 9/2003 | Taylor |
| 6,635,014 B2 | 10/2003 | Starkweather et al. |
| 6,648,821 B2 | 11/2003 | Lebel et al. |
| 6,656,355 B2 | 12/2003 | Sano |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,673,314 B1 | 1/2004 | Burbank et al. |
| 6,673,376 B1 | 1/2004 | Knerr et al. |
| 6,685,831 B2 | 2/2004 | Donig et al. |
| 6,687,546 B2 | 2/2004 | Lebel et al. |
| 6,689,091 B2 | 2/2004 | Bui et al. |
| 6,694,191 B2 | 2/2004 | Starkweather et al. |
| 6,694,334 B2 | 2/2004 | Dulong et al. |
| 6,733,446 B2 | 5/2004 | Lebel et al. |
| 6,733,447 B2 | 5/2004 | Lai et al. |
| 6,740,075 B2 | 5/2004 | Lebel et al. |
| 6,745,903 B2 | 6/2004 | Grandics |
| 6,746,398 B2 | 6/2004 | Hervy et al. |
| 6,746,607 B1 | 6/2004 | Vijayalakshmi et al. |
| 6,749,818 B2 | 6/2004 | Sano et al. |
| 6,752,928 B2 | 6/2004 | Pfeil et al. |
| 6,758,810 B2 | 7/2004 | Lebel et al. |
| 6,758,975 B2 | 7/2004 | Peabody et al. |
| 6,768,425 B2 | 7/2004 | Flaherty et al. |
| 6,787,032 B2 | 9/2004 | Kurome et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,519 B2 | 11/2004 | Lebel et al. |
| 6,820,093 B2 | 11/2004 | De La Huerga |
| 6,854,088 B2 | 2/2005 | Massengale et al. |
| 6,861,033 B2 | 3/2005 | Mullins et al. |
| 6,871,211 B2 | 3/2005 | Labounty et al. |
| 6,873,268 B2 | 3/2005 | Lebel et al. |
| 6,880,034 B2 | 4/2005 | Manke et al. |
| 6,885,288 B2 | 4/2005 | Pincus |
| 6,902,670 B2 | 6/2005 | Ho |
| 6,908,546 B2 | 6/2005 | Smith |
| 6,912,549 B2 | 6/2005 | Rotter et al. |
| 6,913,590 B2 | 7/2005 | Sorenson et al. |
| 6,923,987 B2 | 8/2005 | Kai et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,960,179 B2 | 11/2005 | Gura |
| 6,974,437 B2 | 12/2005 | Lebel et al. |
| 6,976,628 B2 | 12/2005 | Krupa |
| 6,979,306 B2 | 12/2005 | Moll |
| 6,980,958 B1 | 12/2005 | Surwit et al. |
| 6,986,872 B2 | 1/2006 | Taylor |
| 7,024,245 B2 | 4/2006 | Lebel et al. |
| 7,039,878 B2 | 5/2006 | Auer et al. |
| 7,044,927 B2 | 5/2006 | Mueller et al. |
| 7,045,061 B2 | 5/2006 | Nishimura et al. |
| 7,051,002 B2 | 5/2006 | Keresman, III et al. |
| 7,061,831 B2 | 6/2006 | De La Huerga |
| 7,072,769 B2 | 7/2006 | Fletcher-Haynes et al. |
| 7,076,520 B2 | 7/2006 | Nelson et al. |
| 7,077,956 B2 | 7/2006 | Rovatti |
| 7,089,780 B2 | 8/2006 | Sunshine et al. |
| 7,092,796 B2 | 8/2006 | Vanderveen |
| 7,096,072 B2 | 8/2006 | Engleson et al. |
| 7,108,790 B2 | 9/2006 | Collins et al. |
| 7,117,239 B1 | 10/2006 | Hansen |
| 7,122,210 B2 | 10/2006 | Paola |
| 7,156,808 B2 | 1/2007 | Quy |
| 7,161,484 B2 | 1/2007 | Tsoukalis |
| 7,165,221 B2 | 1/2007 | Monteleone et al. |
| 7,171,274 B2 | 1/2007 | Starkweather et al. |
| 7,188,151 B2 | 3/2007 | Kumar et al. |
| 7,194,336 B2 | 3/2007 | DeGianfilippo et al. |
| 7,208,092 B2 | 4/2007 | Micheli |
| 7,216,802 B1 | 5/2007 | De La Huerga |
| 7,231,263 B2 | 6/2007 | Choi |
| 7,238,156 B1 | 7/2007 | Adamczyk |
| 7,241,272 B2 | 7/2007 | Karoor et al. |
| 7,250,619 B2 | 7/2007 | Taylor et al. |
| 7,251,610 B2 | 7/2007 | Alban et al. |
| 7,264,148 B2 | 9/2007 | Tachibana |
| 7,274,799 B2 | 9/2007 | Cohen et al. |
| 7,275,220 B2 | 9/2007 | Brummel et al. |
| 7,290,680 B2 | 11/2007 | Henry et al. |
| 7,292,141 B2 | 11/2007 | Staats et al. |
| 7,300,418 B2 | 11/2007 | Zaleski |
| 7,304,582 B2 | 12/2007 | Robert et al. |
| 7,306,736 B2 | 12/2007 | Collins et al. |
| 7,308,894 B2 | 12/2007 | Hickle |
| 7,309,323 B2 | 12/2007 | Gura et al. |
| 7,315,825 B2 | 1/2008 | Rosenfeld et al. |
| 7,316,648 B2 | 1/2008 | Kelly et al. |
| 7,316,662 B2 | 1/2008 | Delnevo et al. |
| 7,317,967 B2 | 1/2008 | DiGianfilippo et al. |
| 7,319,386 B2 | 1/2008 | Collins, Jr. et al. |
| 7,321,862 B2 | 1/2008 | Rosenfeld et al. |
| 7,343,224 B2 | 3/2008 | DiGianfilippo et al. |
| 7,347,819 B2 | 3/2008 | Lebel et al. |
| 7,356,382 B2 | 4/2008 | Vanderveen |
| 7,369,913 B2 | 5/2008 | Heminway et al. |
| 7,383,196 B1 | 6/2008 | Tang et al. |
| 7,384,410 B2 | 6/2008 | Eggers et al. |
| 7,419,587 B2 | 9/2008 | Valbjoern et al. |
| 7,419,597 B2 | 9/2008 | Brugger et al. |

(56) References Cited

U.S. PATENT DOCUMENTS

| | | |
|---|---|---|
| 7,544,300 B2 | 6/2009 | Brugger et al. |
| 7,749,393 B2 | 7/2010 | Brugger et al. |
| 7,892,423 B2 | 2/2011 | Rohde et al. |
| 7,976,711 B2 | 7/2011 | Brugger et al. |
| 8,029,454 B2 | 10/2011 | Kelly et al. |
| 8,071,055 B2 | 12/2011 | Newcombe |
| 8,177,977 B2 | 5/2012 | Gaignet |
| 8,192,387 B2 | 6/2012 | Brugger et al. |
| 8,216,452 B2 | 7/2012 | Rohde et al. |
| 8,354,029 B2 | 1/2013 | Hank |
| 8,393,690 B2 | 3/2013 | Grant et al. |
| 8,425,767 B2 | 4/2013 | Fava et al. |
| 8,647,290 B2 | 2/2014 | Masala et al. |
| 8,911,390 B2 | 12/2014 | Sternby |
| 9,037,616 B2 * | 5/2015 | Bessette .......... G06Q 90/00 705/2 |
| 9,248,225 B2 | 2/2016 | Demers et al. |
| 9,860,302 B2 | 1/2018 | Wittner et al. |
| 2001/0001237 A1 | 5/2001 | Stroda et al. |
| 2001/0003177 A1 | 6/2001 | Schena et al. |
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0021817 A1 | 9/2001 | Brugger et al. |
| 2001/0025138 A1 | 9/2001 | Bardy |
| 2001/0025156 A1 | 9/2001 | Bui et al. |
| 2001/0027289 A1 | 10/2001 | Treu et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034616 A1 | 10/2001 | Giannini |
| 2001/0037057 A1 | 11/2001 | Bardy |
| 2001/0037079 A1 | 11/2001 | Burbank et al. |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041892 A1 | 11/2001 | Burbank et al. |
| 2001/0041920 A1 | 11/2001 | Starkweather et al. |
| 2001/0042441 A1 | 11/2001 | Purdom et al. |
| 2001/0044588 A1 | 11/2001 | Mault |
| 2001/0044731 A1 | 11/2001 | Coffman et al. |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0010568 A1 | 1/2002 | Rubbert et al. |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0065540 A1 | 5/2002 | Lebel et al. |
| 2002/0067273 A1 | 6/2002 | Jaques et al. |
| 2002/0068015 A1 | 6/2002 | Polaschegg et al. |
| 2002/0072718 A1 | 6/2002 | Brugger et al. |
| 2002/0072733 A1 | 6/2002 | Flaherty |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0131332 A1 | 9/2002 | Kaelin |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiuro |
| 2002/0162778 A1 | 11/2002 | Peabody et al. |
| 2002/0165491 A1 | 11/2002 | Reilly |
| 2002/0169636 A1 | 11/2002 | Eggers et al. |
| 2002/0187940 A1 | 12/2002 | Masuda et al. |
| 2002/0198513 A1 | 12/2002 | Lebel et al. |
| 2003/0000876 A1 | 1/2003 | Kawaguchi |
| 2003/0023177 A1 | 1/2003 | Bardy |
| 2003/0036783 A1 | 2/2003 | Bauhahn et al. |
| 2003/0050621 A1 | 3/2003 | Lebel et al. |
| 2003/0052787 A1 | 3/2003 | Zerhusen |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0065287 A1 | 4/2003 | Spohn et al. |
| 2003/0078534 A1 | 4/2003 | Hochman et al. |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0105424 A1 | 6/2003 | Karoor et al. |
| 2003/0114836 A1 | 6/2003 | Estes et al. |
| 2003/0125611 A1 | 7/2003 | Bardy |
| 2003/0135250 A1 | 7/2003 | Lauman et al. |
| 2003/0139701 A1 | 7/2003 | White et al. |
| 2003/0140929 A1 | 7/2003 | Wilkes et al. |
| 2003/0141368 A1 | 7/2003 | Pascual et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0154108 A1 | 8/2003 | Fletcher-Haynes et al. |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0181851 A1 | 9/2003 | Mann et al. |
| 2003/0182164 A1 | 9/2003 | Shabot et al. |
| 2003/0195397 A1 | 10/2003 | Bardy |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0212379 A1 | 11/2003 | Bylund et al. |
| 2003/0220605 A1 | 11/2003 | Bowman et al. |
| 2003/0225596 A1 | 12/2003 | Richardson et al. |
| 2003/0225728 A1 | 12/2003 | Moura |
| 2004/0010425 A1 | 1/2004 | Wilkes et al. |
| 2004/0039260 A1 | 2/2004 | Bardy |
| 2004/0039264 A1 | 2/2004 | Bardy |

(56) References Cited

U.S. PATENT DOCUMENTS

| | | |
|---|---|---|
| 2004/0051368 A1 | 3/2004 | Caputo et al. |
| 2004/0088374 A1 | 5/2004 | Webb et al. |
| 2004/0111293 A1 | 6/2004 | Firanek et al. |
| 2004/0116862 A1 | 6/2004 | Ray |
| 2004/0117215 A1 | 6/2004 | Marchosky |
| 2004/0121767 A1 | 6/2004 | Simpson et al. |
| 2004/0167465 A1 | 8/2004 | Mihai et al. |
| 2004/0172283 A1 | 9/2004 | Vanderveen et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0193328 A1 | 9/2004 | Zaitsu et al. |
| 2004/0204673 A1 | 10/2004 | Flaherty |
| 2004/0215490 A1 | 10/2004 | Duchon et al. |
| 2004/0220829 A1 | 11/2004 | Baharav et al. |
| 2004/0235446 A1 | 11/2004 | Flaherty et al. |
| 2004/0260233 A1 | 12/2004 | Garibotto et al. |
| 2005/0038680 A1 | 2/2005 | McMahon |
| 2005/0054923 A1 | 3/2005 | Pan |
| 2005/0060202 A1 | 3/2005 | Taylor et al. |
| 2005/0065817 A1 | 3/2005 | Mihai et al. |
| 2005/0070767 A1 | 3/2005 | Maschke |
| 2005/0071194 A1 | 3/2005 | Bormann et al. |
| 2005/0080651 A1 | 4/2005 | Morrison et al. |
| 2005/0177096 A1 | 4/2005 | Bollish et al. |
| 2005/0101901 A1 | 5/2005 | Gura |
| 2005/0102028 A1 | 5/2005 | Arnin et al. |
| 2005/0102167 A1 | 5/2005 | Kapoor |
| 2005/0131340 A1 | 6/2005 | Sorenson et al. |
| 2005/0131741 A1 | 6/2005 | Tang et al. |
| 2005/0133449 A1 | 6/2005 | Sternby |
| 2005/0135306 A1 | 6/2005 | McAllen et al. |
| 2005/0137573 A1 | 6/2005 | McLaughlin |
| 2005/0139651 A1 | 6/2005 | Lim et al. |
| 2005/0143671 A1 | 6/2005 | Hastings et al. |
| 2005/0148890 A1 | 7/2005 | Hastings |
| 2005/0171815 A1 | 8/2005 | Vanderveen |
| 2005/0177395 A1 | 8/2005 | Blomquist |
| 2005/0201345 A1 | 9/2005 | Williamson |
| 2005/0228693 A1 | 10/2005 | Webb et al. |
| 2005/0231374 A1 | 10/2005 | Diem et al. |
| 2005/0234381 A1 | 10/2005 | Niemetz et al. |
| 2005/0246416 A1 | 11/2005 | Blomquist |
| 2005/0267780 A1 | 12/2005 | Ray et al. |
| 2005/0278194 A1 | 12/2005 | Holland et al. |
| 2005/0283385 A1 | 12/2005 | Hunkeler et al. |
| 2006/0015015 A1 | 1/2006 | Kawamoto et al. |
| 2006/0167722 A1 | 1/2006 | Struys et al. |
| 2006/0064020 A1 | 3/2006 | Burnes et al. |
| 2006/0064053 A1 | 3/2006 | Bollish et al. |
| 2006/0065713 A1 | 3/2006 | Kingery |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100907 A1 | 5/2006 | Holland et al. |
| 2006/0106647 A1 | 5/2006 | Brummel et al. |
| 2006/0106649 A1 | 5/2006 | Eggers et al. |
| 2006/0116639 A1 | 6/2006 | Russell |
| 2006/0143051 A1 | 6/2006 | Eggers et al. |
| 2006/0149591 A1 | 7/2006 | Hanf et al. |
| 2006/0173713 A1 | 8/2006 | Petro et al. |
| 2006/0184455 A1 | 8/2006 | Meyer et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0211994 A1 | 9/2006 | Roman et al. |
| 2006/0229551 A1 | 10/2006 | Martinez et al. |
| 2006/0247606 A1 | 11/2006 | Batch |
| 2006/0253301 A1 | 11/2006 | Simms et al. |
| 2006/0258985 A1 | 11/2006 | Russell |
| 2006/0259327 A1 | 11/2006 | Hoag |
| 2006/0277070 A1 | 12/2006 | Hungerford et al. |
| 2007/0033073 A1 | 2/2007 | Tajaliawal |
| 2007/0073266 A1 | 3/2007 | Chmiel et al. |
| 2007/0083386 A1 | 4/2007 | Chuang et al. |
| 2007/0083390 A1 | 4/2007 | Gorup et al. |
| 2007/0088578 A1 | 4/2007 | Hoffman et al. |
| 2007/0124002 A1 | 5/2007 | Estes et al. |
| 2007/0129983 A1 | 6/2007 | Scherpbier et al. |
| 2007/0135866 A1 | 6/2007 | Baker et al. |
| 2007/0156452 A1 | 7/2007 | Batch |
| 2007/0158268 A1 | 7/2007 | DeComo |
| 2007/0163965 A1 | 7/2007 | Wolfe |
| 2007/0179807 A1 | 8/2007 | Nessinger et al. |
| 2007/0185738 A1 | 8/2007 | Anuszewski et al. |
| 2007/0197878 A1 | 8/2007 | Shklarski |
| 2007/0198293 A1 | 8/2007 | Ash et al. |
| 2007/0203753 A1 | 8/2007 | Hasan et al. |
| 2007/0214003 A1 | 9/2007 | Holland et al. |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0255126 A1 | 11/2007 | Moberg et al. |
| 2007/0265879 A1 | 11/2007 | Charlson et al. |
| 2007/0276869 A1 | 11/2007 | Charlson et al. |
| 2007/0278155 A1 | 12/2007 | Lo et al. |
| 2007/0293817 A1 | 12/2007 | Feng et al. |
| 2008/0015895 A1 | 1/2008 | Charlson et al. |
| 2008/0021741 A1 | 1/2008 | Holla et al. |
| 2008/0033360 A1 | 2/2008 | Evans et al. |
| 2008/0033749 A1 | 2/2008 | Blomquist |
| 2008/0034323 A1 | 2/2008 | Blomquist |
| 2008/0045877 A1 | 2/2008 | Levin et al. |
| 2008/0045932 A1 | 2/2008 | Beau et al. |
| 2008/0052317 A1 | 2/2008 | Francis et al. |
| 2008/0059239 A1 | 3/2008 | Gerst et al. |
| 2008/0076969 A1 | 3/2008 | Kraft et al. |
| 2008/0077436 A1 | 3/2008 | Muradia |
| 2008/0086441 A1 | 4/2008 | Wolff et al. |
| 2008/0091466 A1 | 4/2008 | Butler et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0103554 A1 | 5/2008 | Dicks et al. |
| 2008/0114292 A1 | 5/2008 | Rasch-Menges et al. |
| 2008/0126969 A1 | 5/2008 | Blomquist |
| 2008/0133265 A1 | 6/2008 | Silkaitis et al. |
| 2008/0143515 A1 | 6/2008 | Wood et al. |
| 2008/0161754 A1 | 7/2008 | Marano-Ford |
| 2008/0203023 A1 | 8/2008 | Burbank et al. |
| 2008/0208111 A1 | 8/2008 | Kamen |
| 2008/0210606 A1 | 9/2008 | Burbank |
| 2008/0230450 A1 | 9/2008 | Burbank et al. |
| 2009/0008318 A1 | 1/2009 | Anes et al. |
| 2009/0008331 A1 | 1/2009 | Wilt et al. |
| 2009/0012655 A1 | 1/2009 | Kienman et al. |
| 2009/0045121 A1 | 2/2009 | Kabayama et al. |
| 2009/0218285 A1 | 9/2009 | Hank |
| 2010/0018923 A1 | 1/2010 | Rohde et al. |
| 2010/0051546 A1 | 3/2010 | Vuong et al. |
| 2010/0078092 A1 | 4/2010 | Weilhoefer et al. |
| 2010/0137693 A1 | 6/2010 | Porras et al. |
| 2010/0326916 A1 | 12/2010 | Wrazel et al. |
| 2010/0332149 A1 | 12/2010 | Scholpp |
| 2011/0072422 A1 | 3/2011 | Brauer |
| 2011/0100913 A1 | 5/2011 | Minami et al. |
| 2011/0180480 A1 | 7/2011 | Kloeffel et al. |
| 2011/0186521 A1 | 8/2011 | Burbank et al. |
| 2011/0192796 A1 | 8/2011 | Smejtek et al. |
| 2011/0225008 A1 | 9/2011 | Elkouh et al. |
| 2011/0315611 A1 | 12/2011 | Fulkerson et al. |
| 2012/0158882 A1* | 6/2012 | Oehme .................. G16H 30/20 709/213 |
| 2013/0008854 A1 | 1/2013 | Wallace et al. |
| 2013/0062265 A1 | 3/2013 | Balschat et al. |
| 2014/0238912 A1 | 8/2014 | Vincent |
| 2015/0070187 A1* | 3/2015 | Wiesner .................. G16H 40/67 340/870.02 |
| 2015/0082542 A1 | 3/2015 | Hayes et al. |

(56) References Cited

U.S. PATENT DOCUMENTS

| | | | |
|---|---|---|---|
| 2016/0105402 A1* | 4/2016 | Soon-Shiong | H04L 9/3218 713/164 |
| 2017/0203022 A1 | 7/2017 | Burbank et al. | |
| 2021/0027869 A1* | 1/2021 | Sayani | H04L 9/0894 |

FOREIGN PATENT DOCUMENTS

| | | |
|---|---|---|
| DE | 20 02 033 | 8/1970 |
| DE | 29 01 628 | 7/1980 |
| DE | 31 22 756 | 6/1982 |
| DE | 33 07 830 | 6/1984 |
| DE | 34 42 744 | 6/1986 |
| DE | 40 03 452 | 8/1991 |
| DE | 42 08 054 | 10/1992 |
| DE | 41 22 754 | 1/1993 |
| DE | 198 14 695 | 10/1999 |
| DE | 19828923 | 1/2000 |
| DE | 198 54 338 | 6/2000 |
| DE | 19814695 | 9/2001 |
| EP | 0 058 325 | 8/1982 |
| EP | 0 064 393 | 10/1982 |
| EP | 64393 | 11/1982 |
| EP | 0 106 026 | 4/1984 |
| EP | 0 143 340 | 6/1985 |
| EP | 0 143 341 | 6/1985 |
| EP | 152717 | 8/1985 |
| EP | 0 171 550 | 2/1986 |
| EP | 0 233 848 | 8/1987 |
| EP | 0 318 993 | 6/1989 |
| EP | 0 350 675 | 1/1990 |
| EP | 0 373 455 | 6/1990 |
| EP | 0 222 709 | 5/1991 |
| EP | 0243547 | 7/1991 |
| EP | 0 490 212 | 6/1992 |
| EP | 0 501 144 | 9/1992 |
| EP | 0 560 368 | 9/1993 |
| EP | 0402505 | 12/1993 |
| EP | 0 587 251 | 3/1994 |
| EP | 0 720 856 | 7/1996 |
| EP | 0 722 744 | 7/1996 |
| EP | 0498382 | 11/1996 |
| EP | 0778033 | 11/1996 |
| EP | 0 749 328 | 12/1996 |
| EP | 0 776 222 | 6/1997 |
| EP | 0 826 383 | 3/1998 |
| EP | 0 826 384 | 3/1998 |
| EP | 0575512 | 5/1998 |
| EP | 0928615 | 7/1999 |
| EP | 0956876 | 11/1999 |
| EP | 980685 | 2/2000 |
| EP | 0659092 | 10/2000 |
| EP | 0 659 091 | 12/2000 |
| EP | 1 097 724 | 5/2001 |
| EP | 0847769 | 8/2001 |
| EP | 1 277 485 | 1/2003 |
| EP | 1614437 | 1/2006 |
| EP | 2080134 | 5/2008 |
| EP | 2180908 | 5/2010 |
| FR | 2 397 197 | 2/1979 |
| FR | 2 585 251 | 1/1987 |
| GB | 1 408 319 | 10/1975 |
| GB | 2 014 060 | 8/1979 |
| GB | 1 554 810 | 10/1979 |
| GB | 2 061 755 | 5/1981 |
| GB | 2122509 | 1/1984 |
| GB | 2124511 | 2/1984 |
| GB | 2 212 739 | 8/1989 |
| GR | 3 026 703 | 7/1998 |
| JP | 55-32384 | 3/1980 |
| JP | 55-45437 | 3/1980 |
| JP | 55-122559 | 9/1980 |
| JP | 57161511 | 10/1982 |
| JP | 61-25564 | 2/1986 |
| JP | 6-143074 | 6/1986 |
| JP | S61143074 | 6/1986 |
| JP | 4-2060 | 1/1992 |
| JP | 92002060 | 1/1992 |
| JP | 4348757 | 3/1992 |
| JP | 4-384757 | 12/1992 |
| JP | 59-029264 | 2/1994 |
| JP | 07-299455 | 11/1995 |
| JP | 7-299455 | 11/1995 |
| JP | 8-29224 | 2/1996 |
| JP | 8029224 | 2/1996 |
| JP | 96029224 | 2/1996 |
| JP | 9-327511 | 12/1997 |
| JP | 9327511 | 12/1997 |
| JP | 10085324 | 4/1998 |
| JP | H1085324 | 4/1998 |
| JP | 11-137672 | 5/1999 |
| JP | 11137672 | 5/1999 |
| JP | 2000-217908 | 8/2000 |
| JP | 2000-296318 | 10/2000 |
| JP | 200120483 | 12/2000 |
| JP | 2001-270856 | 10/2001 |
| JP | 2003047657 | 2/2003 |
| JP | 2003-513714 | 4/2003 |
| JP | 2011-172961 | 8/2011 |
| JP | 2014520593 A | 8/2014 |
| SE | 1012918 | 3/1981 |
| SE | 1344362 | 6/1984 |
| SU | 1001945 | 3/1983 |
| WO | 1992 018048 | 10/1992 |
| WO | 94/15099 | 7/1994 |
| WO | 9420158 | 9/1994 |
| WO | 95/02559 | 1/1995 |
| WO | 95/17597 | 6/1995 |
| WO | 95/35124 | 12/1995 |
| WO | 9625214 | 8/1996 |
| WO | 9640318 | 12/1996 |
| WO | 97/09074 | 3/1997 |
| WO | 97/47337 | 6/1997 |
| WO | 98/17333 | 4/1998 |
| WO | 98/22165 | 5/1998 |
| WO | 98/23353 | 6/1998 |
| WO | 98/32477 | 7/1998 |
| WO | 99/03519 | 1/1999 |
| WO | 99/06082 | 2/1999 |
| WO | 99/42150 | 8/1999 |
| WO | 00/09182 | 2/2000 |
| WO | 00/20050 | 4/2000 |
| WO | 00/20052 | 4/2000 |
| WO | 00/31967 | 6/2000 |
| WO | 00/50143 | 8/2000 |
| WO | 00/57925 | 10/2000 |
| WO | 00/57926 | 10/2000 |
| WO | 00/57927 | 10/2000 |
| WO | 00/57928 | 10/2000 |
| WO | 00/64510 | 11/2000 |
| WO | 01/37786 | 5/2001 |
| WO | 01/37894 | 5/2001 |
| WO | 01/37895 | 5/2001 |
| WO | 01/37900 | 5/2001 |
| WO | 01/41831 | 6/2001 |
| WO | 01/41832 | 6/2001 |
| WO | 01/41833 | 6/2001 |
| WO | 01/42758 | 6/2001 |
| WO | 01/45769 | 6/2001 |
| WO | 01/47576 | 7/2001 |
| WO | 02/43859 | 6/2002 |
| WO | 2007118235 | 10/2007 |
| WO | 2008138311 | 11/2008 |
| WO | 2011069110 | 6/2011 |
| WO | 2012120078 | 9/2012 |
| WO | 2012129501 | 9/2012 |

OTHER PUBLICATIONS

Written Opinion for corresponding International Application PCT/US2009/031809 dated Oct. 19, 2009.

(56) References Cited

OTHER PUBLICATIONS

Japanese Office Action dated Dec. 14, 2012 for related Application No. 2011-100145—corresponding communication indicates no references cited in JP Office Action (1 page).
Fresenius 90/2 Peritoneal Therapy Cycler, Articile, written by Fresenius SA, dated Jul. 1993—6 pages.
Notice of Reasons for Rejection dated Dec. 5, 2017 in corresponding JP Application No. 2013-257132.
European Search Report—EP Application No. 16176496 dated Mar. 21, 2017—13 pages.
European Communication—EP Application No. 09710209.9 dated Mar. 20, 2015—6 pages.
Search and Examination Report dated Jul. 29, 2014 for related GB Appl. No. 1322331.8.
Office Action for Mexican Patent Application No. MX/a/2010/008961 received Apr. 22, 2013.
International Search Report for PCT/US2017/031405 dated Sep. 26, 2017—7 pages.
Written Opinion of the International Searching Authority for PCT/US2017/031405 dated Sep. 26, 2017—13 pages.
International Search Report for PCT/US2017/031400 dated Sep. 26, 2017—7 pages.
Written Opinion of the International Search Authority for PCT/US2017/031400 dated Sep. 26, 2017—14 pages.
International Search Report for PCT/US2017/031396 dated Jul. 27, 2017—6 pages.
Written Opinion of the International Search Authority for PCT/US2017/031396 dated Jul. 27, 2017—7 pages.
U.S. Appl. No. 15/195,801, filed Jun. 28, 2016.
Japanese Office Action received Jun. 13, 2013 for Japanese Application No. 2011-100145.
Japanese Office Action dated Feb. 18, 2014 for related Japanese Appln. No. 2013-051434.

\* cited by examiner

MEDICAL DEVICE SYSTEM INCLUDING INFORMATION TECHNOLOGY INFRASTRUCTURE HAVING SECURE CLUSTER DOMAIN SUPPORTING EXTERNAL DOMAIN

PRIORITY CLAIM

The present application is a National Phase filing of International Application No. PCT/EP2017/081763, filed Dec. 7, 2017, which claims priority to Swedish Application No. 1651699-9, filed Dec. 21, 2016, the entire contents of each of which are incorporated herein by reference and relied upon.

BACKGROUND

The present disclosure relates generally medical device systems and more particularly to the managing and running of an information technology ("IT") infrastructure with connection to external systems like clinic information systems ("CIS"), billing systems, laboratories, and the like.

IT connectivity for medical systems was introduced originally to only a selected set of medical providers and was strictly proprietary. Eventually, medical IT systems gradually started to rely on standardized solutions, which were considered advantageous from cost and development perspectives. On the downside, where responsibility resided before with the proprietary system providers, standardized solutions split the responsibility for the reliability of the IT systems onto several parties, the major responsibilities being delegated to the associated equipment manufacturer, the CIS manufacturer, and IT professionals.

The complexity involved in managing the infrastructure of a medical device IT system is considerable and, in general, only larger clinics may afford the cost and competence to setup and maintain such a system running with the reliability and availability required in a health care environment. The result is that progress in using IT-based support to increase the efficiency in medical device settings, such as dialysis clinics, has been slow. Indeed, many would say that little progress has been seen over the last thirty years in the health care environment when compared to the explosive development of today's personal computing and smart mobile communication devices.

The burden on the clinic is further increased by the fact that the clinic is ultimately responsible from a quality management and risk analysis perspective when combining all subsystems and equipment into a unit. The responsibility imposes expectations on the clinic to have access to qualified personnel for performing such quality and risk management evaluations, since most equipment and software manufacturers will refrain from assuming such responsibilities when their products are combined with other products, or integrated in a system in which the software manufacturers have no prior or upfront knowledge.

To summarize, most medical treatment settings (e.g., dialysis clinics) today recognize the potential of IT systems in reducing errors, documentation workload and other administration workload. The clinics also recognize the cost and complexity of managing different IT solutions and that off-the-shelf support for integrating such systems is very limited. That is, the clinics realize that they will shoulder the burden of implementing and maintaining an IT solution. Most clinics however do not have and cannot afford dedicated IT personnel.

While there is a widespread desire to use IT for therapy management, many electronic medical record systems in place do not meet the needs from either a data structure or a reporting perspective. Existing systems are accordingly perceived as lacking understanding for the medical user's needs in the context of clinic workflow management.

An improved IT solution for medical treatment settings, e.g., dialysis clinics, in which there is a large data management need but a relatively small IT budget, is needed accordingly.

SUMMARY

The medical device information technology ("IT") system and methodology of the present disclosure is applicable, for example, to medical devices such as those for: plasmapheresis, hemodialysis ("HD"), hemofiltration ("HF") hemodiafiltration ("HDF"), and continuous renal replacement therapy ("CRRT") treatments. The medical device IT system described herein is also applicable to peritoneal dialysis ("PD"), intravenous drug delivery, and nutritional fluid delivery. These modalities may be referred to herein collectively or generally individually as medical fluid delivery, however, the IT system is not limited to medical fluid delivery and instead may involve medical devices generally. The medical devices may house components needed to deliver medical fluid, such as one or more pump, plural valves, a heater if needed, online medical fluid generation equipment if needed, plural sensors, such as any one, or more, or all of pressure sensors, conductivity sensors, temperature sensors, air detectors, blood leak detectors, and the like, a user interface, and a control unit, which may employ one or more processor and memory to control the above-described equipment. The medical fluid delivery device may also include one or more filter, such as a dialyzer or hemofilter for cleansing blood and/or an ultrafilter for purifying water, dialysis fluid, or other fluid.

The medical device IT system and methodology of the present disclosure may be used with medical devices located in a clinic/hospital or with home-based medical devices. One suitable hemodialysis machine for a clinical setting is described in U.S. Pat. No. 8,647,290, issued Feb. 11, 2014, entitled "Hemodialysis or Hemo(dia)filtration Apparatus and a Method for Controlling a Hemodialysis or Hemo(dia) filtration Apparatus", filed May 26, 2008. One suitable CRRT machine for a hospital or clinical setting is described in U.S. Pat. No. 8,911,390, issued Dec. 16, 2014, entitled "Multipart Fluid System And A System For Regional Citrate Anticoagulation In An Extracorporeal Blood Circuit", filed Mar. 31, 2010. One suitable home system is described in U.S. Pat. No. 8,029,454, issued Oct. 4, 2011, entitled "High Convection Home Hemodialysis/Hemofiltration and Sorbent System", filed Nov. 4, 2004, assigned to the assignee of the present application. Another such home system is described in U.S. Pat. No. 8,393,690, issued Mar. 12, 2013, entitled "Enclosure for a Portable Hemodialysis System", filed Aug. 27, 2008. One suitable peritoneal dialysis system that may be used at home or in a clinic is described in U.S. Pat. No. 9,248,225, issued Feb. 2, 2016, entitled "Medical Treatment System and Methods Using a Plurality of Fluid Lines", filed Jan. 23, 2009. The entire contents of each of the above references are incorporated herein by reference and relied upon.

Each of the above types of medical devices may be considered to be a node in a cluster of multiple nodes, which share a common distributed database. Each node of the cluster shares its data (e.g., (i) data concerning its programmed operating parameters, (ii) data gathered from a treatment such as medical device output data, event data, and patient data, and (iii) any other relevant data) with each other node of the cluster. To share its data, the cluster may be configured such that the nodes (i) push their data to each other, (ii) pull their data from each other, or (iii) push and pull data from each other. Further, to share its data, the cluster may be configured such that (a) the nodes each send their data to each other node using (i), (ii) or (iii) or (b) one or more hub node may be provided that collects data from a subset of nodes, shares the data along with its own data within the subset, passes the collected data along with its own data to any other existing hub node for distribution within the other node's subset, and receives collected data from any other hub node for distribution within its own subset, using (i), (ii) or (iii).

Regardless of how information is shared within the cluster or distributed database, the information and information sharing is secure and complete. The information is secure for multiple reasons. First, only cluster compatible and certified nodes are connected to the cluster, and only these nodes may share data. Managed exceptions to this rule are described below. Second, software for the cluster is in one embodiment proprietary, so that outside devices not having the proprietary software cannot communicate with the nodes even if somehow connected to the same network as the nodes of the cluster. The proprietary software may have standardized components, e.g., may use open source software, but the overall software is proprietary.

The cluster is in one embodiment provided by the medical device manufacturers. The secure distributed database is deployed as part of each medical device participating as nodes in the cluster. The cluster compatible medical devices connect in a network and automatically form the shared or distributed database of the present disclosure, which may be formed around a physical database (e.g., hard disk-based) residing in each physical medical device. Discussed below are many functions that the cluster of nodes may control. The cluster of devices (nodes) designed for running as cluster member nodes assumes the majority of the responsibility for handling the complexities associated with an open IT infrastructure and is accordingly an attractive option for clinics and any other medical device setting in which there is a large data management need but a relatively small IT budget. Some responsibility may still reside with the clinic, such as providing cabling and other hardware.

The cluster and its nodes may be said to form a cluster domain. It is expected that most if not all clinics or other medical device settings will have some sort of computer network upon which nurses, clinicians and technicians may use to run pertinent software, such as third party clinical software, billing software, accounting software, etc. Any of this software outside of the cluster domain may be said to form an external domain.

Some of the external domain software may have a need for at least some of the data shared within the distributed database. Additionally, depending upon what functions are handled within the cluster domain, there may be a need for the distributed database to receive data from and deliver data to the external domain. To do so, it is contemplated to create or designate one or more nodes of the distributed data base as an access node. Each access node in an embodiment has an internal part and an external part, which may only communicate with each other through one or more controlled interface, such as a memory manager. The external part of the access node interfaces with the external domain, while internal part of the access node interfaces with the cluster domain. The cluster access nodes may be said to form an interface domain between the open external domain and the internal cluster domain.

It is contemplated to provide three different types of access options. A first type of access option is an access node, which is a distributed database access node. This access node maintains the shared database formed between all the other nodes. The distributed database access node may or may not add data to the shared database but in either case receives all data from all other nodes generating data and permanently storing the data. The distributed database access node enables a client device to receive data from the shared database and to add data to the shared database. While the access nodes are generally described as being different from the medical devices of the cluster, it is contemplated that a medical device may also provide access capabilities and therefore also form an access node.

A second type of access option is also an access node, but which is a conversion only node or non-distributed database access node. A non-distributed database access node does not contain the shared database and is instead limited to allowing a client device to interact functionally with a cluster node. For example, it may be desired to send from a weight scale a patient's weight data wired or wirelessly to the cluster via the non-distributed database access node. In an embodiment, the non-distributed database node connects to a distributed database node and transfers its information to that node. The transferred information is shared with the rest of the distributed database at the next distributed database update. The weight data along with a patient identifier may then be recalled by whichever node or medical device has need for the weight data, e.g., the node or medical device treating the patient that day. The conversion only access node enables a secure transfer of the weight data to the cluster of nodes but does not itself contain the distributed database.

Besides the two types of physical access nodes, it is contemplated to provide a third type of interface between the distributed database domain and the external domain, which may be referred to as a virtual access node. The access node is considered virtual because there is no additional hardware involved. The virtual node may for example be software in a doctor's or clinician's computer that runs in its own open network separated from the distributed database. The doctor or clinician's computer and the lab technician's computer may run software that needs to or benefits from sharing information with the distributed database. Such software might for example require data from the lab technician's computer, e.g., patient test results. While it is contemplated that the doctor or clinician's computer be able to send service requests via an access node to invoke operational routines running in the distributed database, it may alternatively be possible and perhaps desirable to enable the doctor's computer to access the distributed database virtually with the assurance that the doctor's computer is protected enough to do so. For example, the security may be provided via a virtual private network ("VPN") between the doctor's computer and the part of a virtual access node that resides inside a medical device.

The medical device IT system and methodology of the present disclosure reduces the overall complexity of managing and running an IT infrastructure, while offering full flexibility to connect to external systems (a CIS, billing systems, laboratories, etc.) deployed within or outside a medical device clinic. The IT system and methodology is hidden and controlled at a single responsible part (the cluster configuration and its associated distributed database) for critical areas like reliability, availability, security, safety and integrity, while at the same time providing access to services needed in the clinic from a process, staff and patient perspective. The IT system and methodology is able to integrate patient related medical information stored in the distributed database with the clinic's overall medical record system and with information used and produced by equipment at the patient's bedside, before, during and/or after treatment.

The medical device IT system and methodology of the present disclosure enables data to flow both ways, in real time, e.g., between outside medical equipment and the medical devices of the cluster, enabling, for example, correct dialysis equipment setup prior to treatment based on physician's prescriptions and on information generated at the bedside, e.g., under the guidance of nurses and other dialysis caregiver staff, before, during and/or after treatment. Conversely, it may be desired that actual treatment result information from medical equipment, e.g., events (e.g., alarms, alerts) generated and documented on the equipment, and nurse's notes or inputs associated with a treatment be transmitted back to the CIS for short and/or long term medical evaluation.

The complexity of running current "open" IT structures in the clinics originates from maintaining an infrastructure of application servers with server software, database servers, backup servers (physically separated from the servers), IT network (wired or wireless, cabling and routers) and client computers with client software. Integrating such infrastructure within medical device equipment to collectively form a distributed database, in combination with supporting proprietary connectivity equipment (access nodes), in a "closed" cluster configuration with access to/from external systems (e.g. a CIS or any other information management system) causes the main responsibility for the overall reliability of such an infrastructure to be limited and confined within the well-controlled realm of the medical equipment and its integrated distributed database.

The advantages of the medical device IT system and methodology of the present disclosure are applicable to home treatment and other external scenarios as well. There may for example be a separate cluster of nodes forming a virtual network of, e.g., home dialysis machines, or a mixture of in-center and home dialysis machines. The clinic responsible for the home-based medical devices may still benefit from the synchronization mechanisms and other services offered by the cluster. The main exception is the control of the transport infrastructure, which in case of home patients cannot be claimed to be under the control of the cluster configuration. This may affect availability and performance since disturbances in such infrastructure is beyond control from the cluster. However, most other benefits of the cluster configuration in addition to synchronization will still be available, e.g. safety, security, integrity and information exchange will still be available, albeit subject to data rates offered by the transport chain between clinic and the patient home environment.

Cluster inclusion of medical devices external to a clinic or hospital may be valuable in a situation in which a patient normally treated in a clinic is instead treated temporarily outside the clinic (e.g., home, work trip or vacation). The system of the present disclosure may ensure that all medical devices belonging to a clinic are configured in the same way (e.g., technically), regardless if they are used inside or outside of the clinic. In an embodiment, medical devices or nodes used at the patient's home location are given restricted access to the shared database, so that the patient may only see his or her own data and the information needed to setup and run a treatment. The data generated by the external treatment is added to the shared database. The device is therefore not necessarily operating "offline" from the database when operating outside of the hospital or clinic.

In light of the disclosure herein and without limiting the disclosure in any way, in a first aspect of the present disclosure, which may be combined with any other aspect listed herein unless specified otherwise, a medical device system includes: a cluster including a plurality of nodes and running proprietary software; a plurality of medical devices implementing at least some of the nodes; at least one of the nodes being an access node; a distributed database shared along the cluster and hosted by at least some of the nodes; and at least one external equipment outside the cluster, the at least one external equipment running software different than the proprietary software and able to at least one of (i) write to, or (ii) read from, at least some of the distributed database via the access node.

In a second aspect of the present disclosure, which may be combined with any other aspect listed herein unless specified otherwise, the at least one access node is provided separately from the medical devices.

In a third aspect of the present disclosure, which may be combined with any other aspect listed herein unless specified otherwise, the at least one access node is provided with one the medical devices.

In a fourth aspect of the present disclosure, which may be combined with any other aspect listed herein unless specified otherwise, the at least one access node does not host the distributed database.

In a fifth aspect of the present disclosure, which may be combined with any other aspect listed herein unless specified otherwise, the at least one external equipment is a first external equipment, and which further includes a virtual access node of the cluster formed via a second external equipment, the virtual access node providing a secure data exchange environment so as to ensure security of the cluster operating with the second external equipment.

In a sixth aspect of the present disclosure, which may be combined with the fifth aspect in combination with any other aspect listed herein unless specified otherwise, the secure data exchange environment includes a secure channel such as a virtual private network.

In a seventh aspect of the present disclosure, which may be combined with any other aspect listed herein unless specified otherwise, the at least one external equipment is configured to deliver data to the distributed database, the data used by one of the medical devices implementing one of the nodes for treatment.

In an eighth aspect of the present disclosure, which may be combined with any other aspect listed herein unless specified otherwise, the plurality of medical devices are of a same treatment type.

In a ninth aspect of the present disclosure, which may be combined with any other aspect listed herein unless specified otherwise, the plurality of medical devices are treating a same patient.

In a tenth aspect of the present disclosure, which may be combined with any other aspect listed herein unless specified otherwise, the distributed database is populated by (i) each of the nodes that produces data pushing its data to other nodes, (ii) each of the nodes having distributed database pulling data from other nodes, or (iii) a combination of (i) and (ii).

In an eleventh aspect of the present disclosure, which may be combined with any other aspect listed herein unless specified otherwise, a medical device system includes: a cluster including a plurality of nodes; each of a set of the nodes implemented by a medical device; a distributed database hosted by each of the medical devices; at least one first access node that hosts the distributed database; at least one second access node provided separately from the distributed database; and at least one external equipment outside of the cluster, the at least one external equipment able to at least one of (i) write to, or (ii) read from, the distributed database via the at least one first access node or the at least one second access node.

In a twelfth aspect of the present disclosure, which may be combined with the eleventh aspect in combination with any other aspect listed herein unless specified otherwise, the at least one first access node and the at least one second access node are separate from the medical devices.

In a thirteenth aspect of the present disclosure, which may be combined with the eleventh aspect in combination with any other aspect listed herein unless specified otherwise, the at least one first access node and the at least one second access node are provided with or operate with a user interface.

In a fourteenth aspect of the present disclosure, which may be combined with any other aspect listed herein unless specified otherwise, a medical device system includes: a cluster including a plurality of nodes; a plurality of medical devices implementing at least some of the nodes; at least one of the nodes being an access node including an external part and an internal part; a distributed database provided along the cluster and hosted by at least some of the nodes, the distributed database, if stored by the at least one access node, associated with the internal part of the access node; and at least one external equipment outside the cluster, the at least one external equipment able to at least one of (i) write to, or (ii) read from, at least some of the distributed database via the external part of access node.

In a fifteenth aspect of the present disclosure, which may be combined with the fourteenth aspect in combination with any other aspect listed herein unless specified otherwise, the external part and the internal part are separated by a processing and memory manager that knows how to (i) place data into the external part coming from the internal part and (ii) place data into the internal part coming from the external part.

In a sixteenth aspect of the present disclosure, which may be combined with any other aspect listed herein unless specified otherwise, a medical device system includes: a cluster including a plurality of nodes; a plurality of medical devices implementing at least some of the nodes, each medical device including processing and memory configured to perform a medical procedure; and a distributed database shared along the cluster by at least some of the nodes, the distributed database deployed on the plurality of medical devices, the distributed database separated from the processing and memory configured to perform the medical procedure by a processing and memory manager that knows how to (i) place data into the processing and memory configured to perform the medical procedure coming from the distributed database and (ii) place data into the distributed database coming from the processing and memory configured to perform the medical procedure.

In a seventeenth aspect of the present disclosure, which may be combined with the sixteenth aspect in combination with any other aspect listed herein unless specified otherwise, the processing and memory configured to perform the medical procedure are configured to initiate communication with the distributed database via the processing and memory manager.

In an eighteenth aspect of the present disclosure, which may be combined with the sixteenth aspect in combination with any other aspect listed herein unless specified otherwise, the distributed database is located in a cluster control part of the medical device that is separate from the processing and memory configured to perform the medical procedure located in a therapy control part of the medical device, the cluster control part separated from the therapy control part by the processing and memory manager.

In a nineteenth aspect of the present disclosure, which may be combined with any other aspect listed herein unless specified otherwise, a medical device system includes a medical device system (110) including: a cluster (10) including a plurality of nodes (12); a plurality of medical devices implementing at least some of the nodes (12); a distributed database (14) shared along the cluster (10) and hosted by the plurality of medical devices; an external equipment (50) outside the cluster (10); and a virtual access node (100) of the cluster (10) formed with the external equipment (50) and one of the medical devices, the virtual access node (100) providing a secure data exchange environment so as to ensure the security of the distributed database (14) when the external equipment (50) writes to, or (ii) reads from, the medical device.

In a twentieth aspect of the present disclosure, which may be combined with the nineteenth aspect in combination with any other aspect listed herein unless specified otherwise, the medical device includes a first virtual access node interface and the external equipment includes a second virtual access node interface, and wherein the secure data exchange environment includes a secure channel such as a virtual private network interfacing with the virtual access node interfaces.

In a twenty-first aspect of the present disclosure, any of the structure and functionality disclosed in connection with FIGS. 1 to 15 may be combined with any of the other structure and functionality disclosed in connection with FIGS. 1 to 15.

In light of the present disclosure and the above aspects, it is therefore an advantage of the present disclosure to provide an improved medical information technology ("IT") system in which connectivity is integrated into the associated medical devices.

It is another advantage of the present disclosure to reduce the clinic's cost of ownership for an IT connectivity solution in a health care environment, and wherein responsibility for operation is centralized around a cluster of nodes having a well defined scope.

It is a further advantage of the present disclosure to improve reliability, availability and correctness of an IT connectivity solution in a health care environment.

It is still another advantage of the present disclosure to provide an IT connectivity solution in a health care environment that is easy for caregiver staff, e.g., nurses and technicians, to use, and which reduces overhead work.

It is still a further advantage of the present disclosure to provide an IT connectivity solution in a health care environment that promotes and supports the needs of at least one of a care giver (remote alarms, instant access, bidirectional information flow), a physician, whose primary concerns are the welfare of and benefits for the patient (prescription updates, access to information even if the medical devices belonging to the cluster are not available, real time retrieval of patient data), an IT technician (reduced IT complexity, responsibility held at least in part by the medical device maker), a service technician (software installs and updates may be cluster wide, historical data readily available, early warning diagnostics), and/or an administrator (easy to set and implement clinical preferences, run reports and obtain statistics, easy to schedule medical devices for treatments, easy to track patient data).

Further still, it is an advantage of the present disclosure to provide an IT connectivity solution that provides all updates, instantly, to all nodes, with low risk of distorted information.

It is yet another advantage of the present disclosure to provide an IT connectivity solution that is two-way between a secured, real time distributed medical device domain and an outside, open external domain, and which has malware immunity.

It is yet a further advantage of the present disclosure to provide scalability to a clinic or other medical device setting in which a cluster of medical devices may operate alone, with a lesser set of external devices upon installation, and with an expanded set of external databases in the future if desired.

Still a further advantage of the present disclosure is to provide an IT connectivity solution that enables a medical device node or access node that is temporarily disconnected (by choice or by accident) from the cluster of nodes to still have access to the distributed database as it existed at the time of disconnection and to be updated upon reconnection to the cluster of nodes.

Moreover, it is an advantage of the present disclosure to provide a medical device IT connectivity solution that provides good overall reliability regarding at least one of data availability, correctness, security, safety, integrity and/or usability.

The advantages discussed herein may be found in one, or some, and perhaps not all of the embodiments disclosed herein. Additional features and advantages are described herein, and will be apparent from, the following Detailed Description and the figures.

DETAILED DESCRIPTION

The examples described herein are applicable to any type of medical device, for example, medical devices that deliver a medical fluid, such as blood, dialysis fluid, substitution fluid or an intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as renal failure therapy. The medical devices may alternatively be drug delivery or nutritional fluid delivery medical devices, such as large volume peristaltic type pumps or syringe pumps. The medical devices may have any one or more of: one or more pump, plural valves, a heater if needed, online medical fluid generation equipment if needed, plural sensors, such as any one, or more, or all of pressure sensors, conductivity sensors, temperature sensors, air detectors, blood leak detectors, and the like, a user interface, and a control unit, which may employ one or more processor and memory to control the above-described equipment. The medical device may also include one or more filter, such as a dialyzer or hemofilter for cleansing blood and/or an ultrafilter for purifying water, dialysis fluid, or other fluid.

The medical devices in many instances include a reusable part operating with a disposable part. The reusable part may (e.g., online blood treatment dialysis machines) or may not (e.g., peritoneal dialysis machines, CRRT machines, drug and nutritional fluid delivery machines) carry treatment fluid. The disposable part may carry blood (blood treatment including CRRT machines) or treatment fluid (peritoneal dialysis machines, CRRT machines, drug and nutritional fluid delivery machines).

Figure 1:
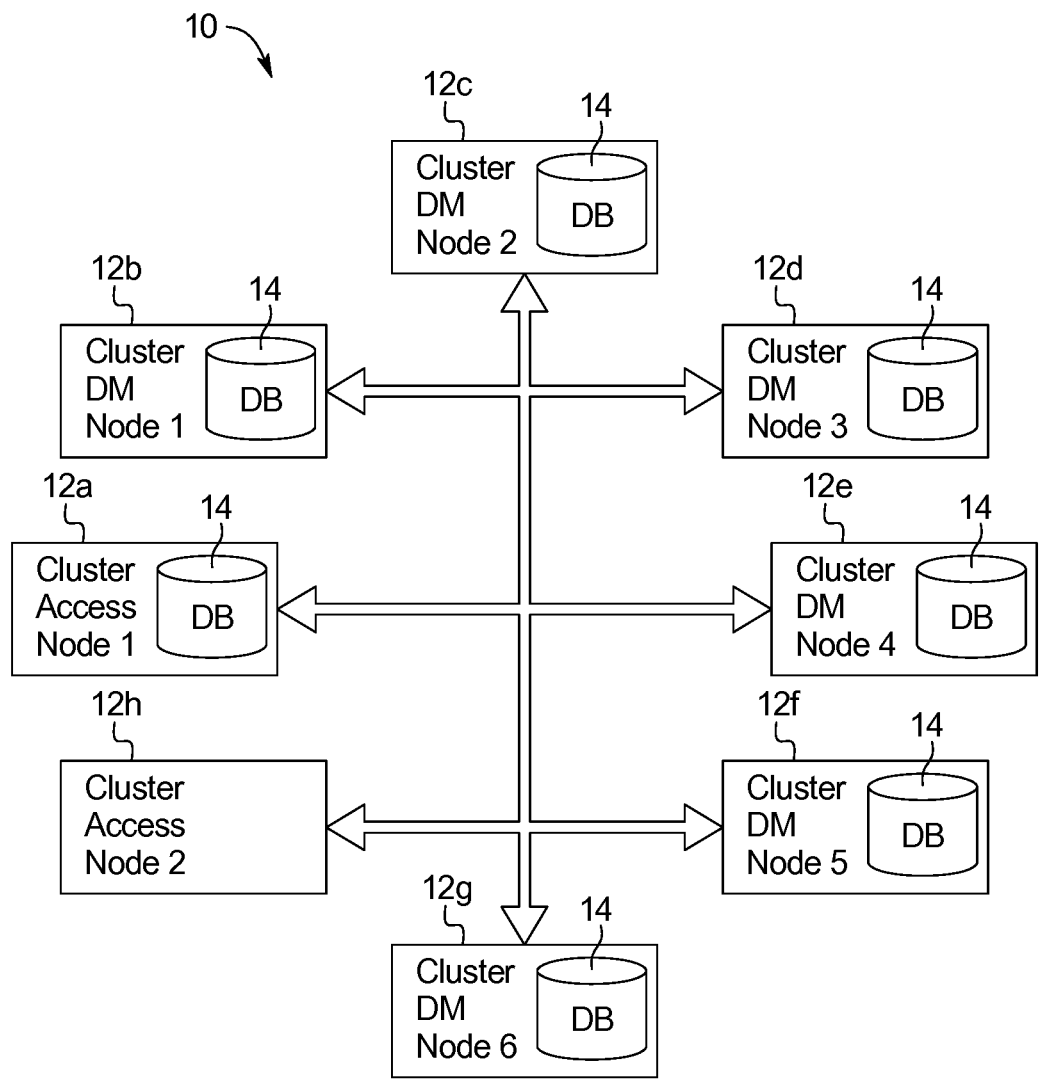
FIG. 1 is a schematic view illustrating one embodiment of a cluster of nodes sharing a distributed database of the present disclosure.

Referring now to the drawings and in particular to FIG. 1, a cluster of nodes 10 is illustrated. Cluster 10 includes a plurality of nodes 12*a* to 12*h* (referred to herein collectively as nodes 12 or generally individually as node 12). Nodes 12 may be represented by any of the medical devices described above. Any of nodes 12 may alternatively be a computer. Most of the nodes of cluster 10 share a common set of data or distributed database 14. As discussed in detail below, access node 12*h* does not possess or share distributed database 14.

Distributed database 14 is the combination of all data inputted to and generated at each of nodes 12, including data generated by non-distributed database node 12*h*. That is, even though node 12*h* does not share distributed database 14, data may still come in through non-distributed database node 12*h* or be generated by node 12*h*, which becomes part of distributed database 14 shared by nodes 12*a* to 12*g*.

Many embodiments for how nodes 12*a* to 12*g* may share their data are set forth in copending Patent Cooperation Treaty Application PCT/EP2016/064392, having an international filing date of 22 Jun. 2016, and a common applicant with the present disclosure, the entire contents of which are incorporated herein by reference and relied upon. In general each node 12 of cluster 10 shares its data (e.g., (i) data concerning its programmed operating parameters, (ii) data gathered from a treatment such as medical device output data, event data, and patient data, and (iii) any other relevant data) with each other node 12 of cluster 10, except certain access nodes, such as node 12*h*. To share its data, cluster 10 may be configured such that nodes 12 (i) push their data to each other, (ii) pull their data from each other, or (iii) push and pull data from each other. Further, to share its data, cluster 10 may be configured such that (a) nodes 12 each send their data to each other node using (i), (ii) or (iii) or (b) one or more hub node may be provided that collects data from a subset of nodes, shares the data along with its own data within the subset, passes the collected data along with its own data to any other existing hub node for distribution within the other node's subset, and receives collected data from any other hub node for distribution within its subset, using (i), (ii) or (iii).

The nodes of cluster 10 run on proprietary software and access to distributed database 14 is limited to that described below. The software may be built using off the shelf components, such as open source software, but the overall product is proprietary. Thus, even if cluster 10 is somehow improperly accessed or hacked, access to distributed database data 14 is difficult without the proprietary software (e.g., software developed in-house by the medical device manufacturer, which may use publically available software, such as open source software, but which itself is not publically available). Cluster 10 may therefore, within a closed environment, be trusted handle all aspects regarding the complexities associated with existing clinics running open IT infrastructures. Such complexities may include assuming: (i) required server (service) and synchronization roles, (ii) database deployment, (iii) network solutions on all levels (except perhaps on a physical and link layer level, where there is an option of either running on an existing/shared hardware infrastructure or running a virtual private network on existing clinic IT hardware solutions), and (iv) backup server roles as each node 12 having common set of data 14 acts as a backup device (except a requirement that a back-up server has to be physically separated from any other device).

By integrating information technology ("IT") infrastructure support within a medical device, in combination with supporting proprietary connectivity equipment, in a "closed" cluster configuration with limited access to/from cluster-external systems (e.g., a client information system ("CIS") or any other information system), the responsibility for the overall reliability of such IT infrastructure is restricted and confined within the well-controlled realm of the medical equipment, e.g., medical fluid delivery device nodes 12.

Figure 2:
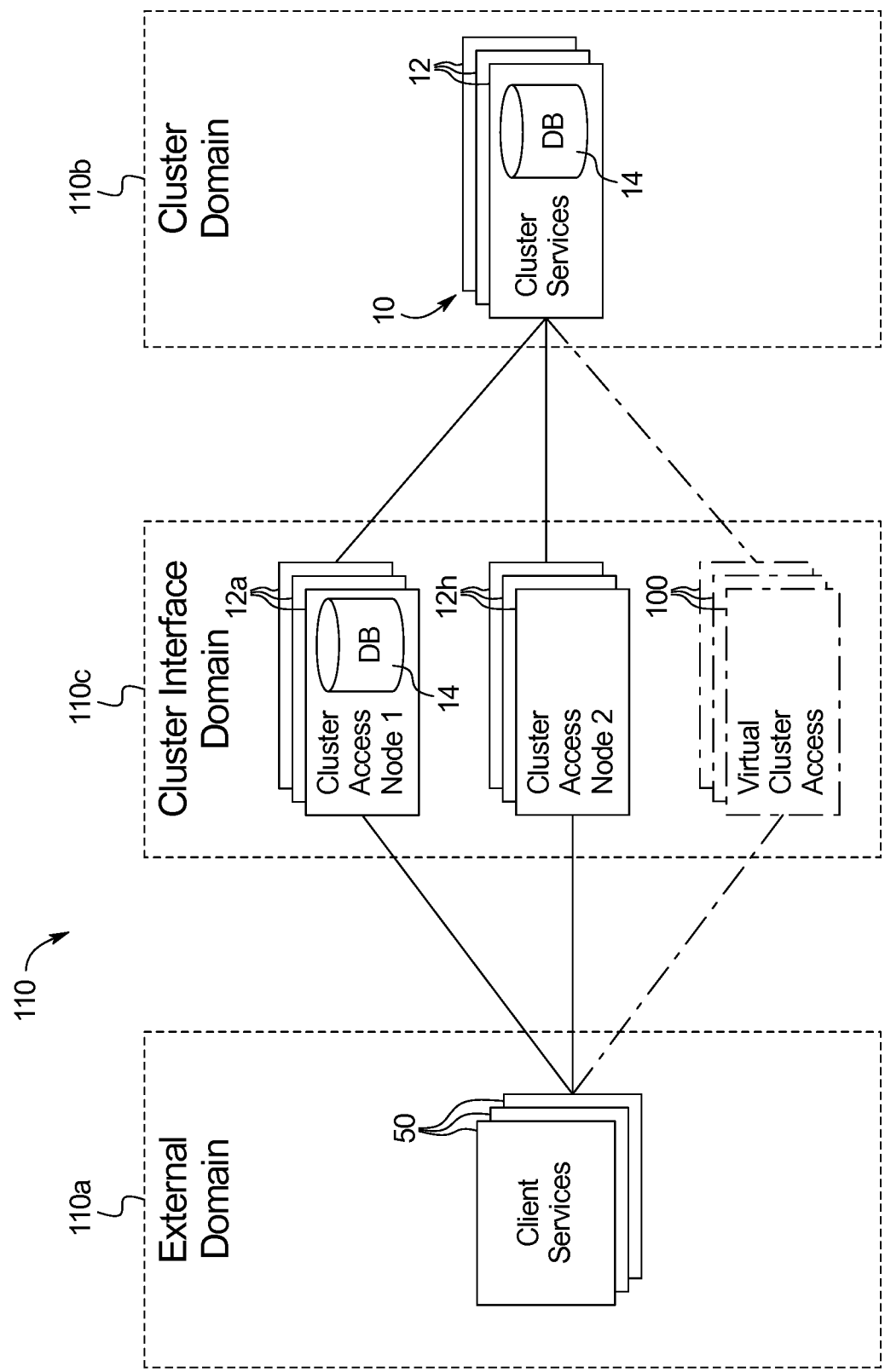
FIG. 2 is a schematic illustration of one embodiment of an overall medical device information technology ("IT") system including a cluster of nodes forming a cluster domain that communicates with an open external domain via an interface domain.
Figure 3:
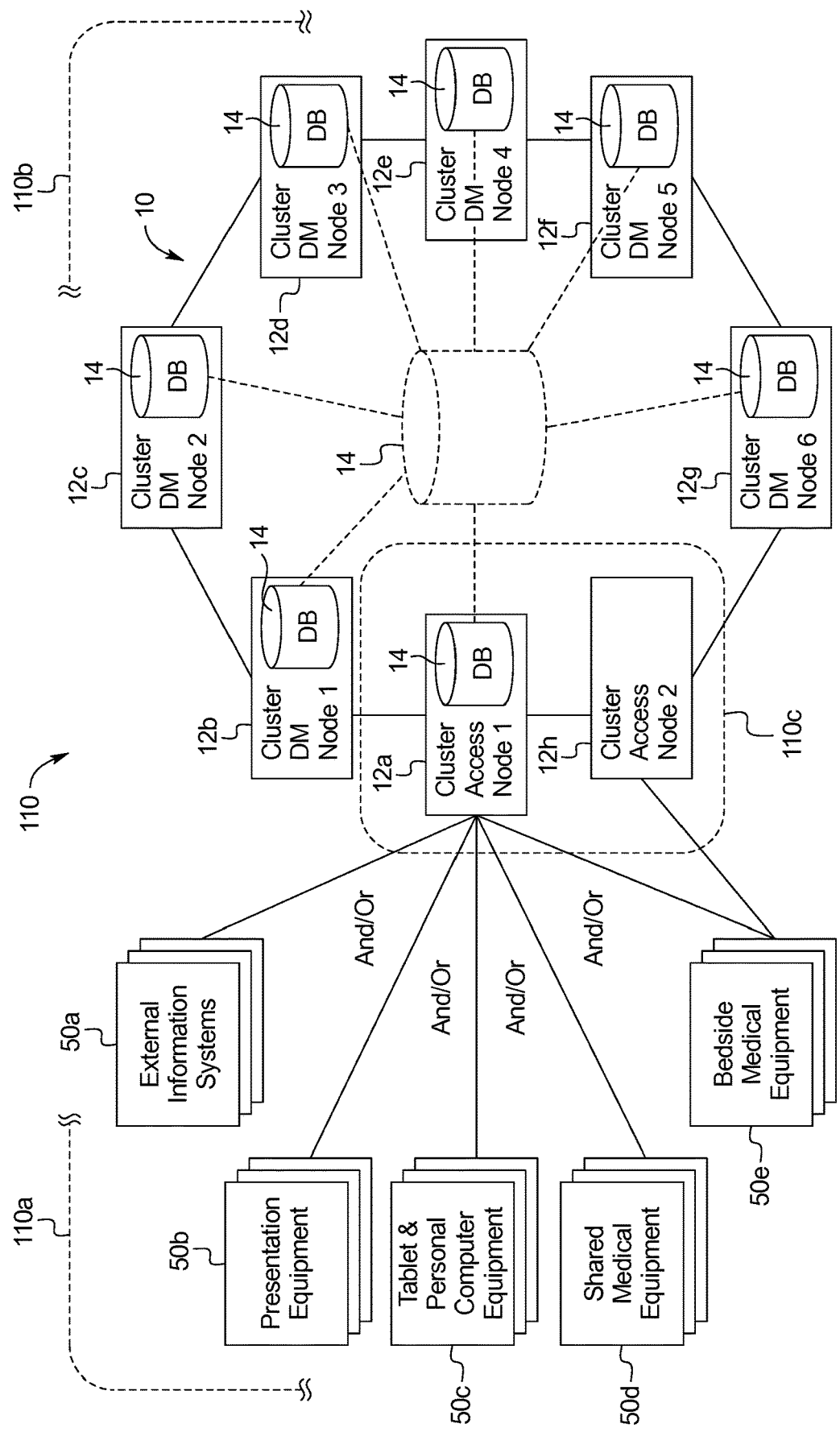
FIG. 3 is a schematic view of one embodiment of an overall medical device IT system that includes a cluster of nodes sharing a distributed database interfacing with plural external entities via multiple access nodes of the cluster.

Referring now to FIGS. 2 and 3, cluster 10 of FIG. 1 is illustrated as being part of an overall medical device information technology ("IT") system 110. FIG. 2 illustrates that system 110 includes an external domain 110*a*, a cluster domain 110*b*, and an interface domain 110*c*, which links external domain 110*a* to cluster domain 110*b*. In FIG. 2, cluster 10 of FIG. 1 is illustrated as being part of cluster domain 110*b*. There may be multiple clusters 10 forming cluster domain 110*b*. For example, there may be different clusters 10 for the different types of medical devices described above at nodes 12.

Cluster domain 110*b* represents core functionality of the cluster database services and infrastructure. Cluster domain 110*b* handles the transfer and conversion of information flow in both cluster 10 inbound and outbound directions between it and external domain 110*a*. As discussed above, each node 12 (except node 12*h*) of cluster 10 holds shared data 14. Each node 12 of each cluster 10 (there may be more than one cluster 10 in domain 110*b*) of cluster domain 110*b* is mutually synchronized, which allows for arbitrary member nodes 12 to be shut down while still maintaining external access to the services and information of cluster 10.

Each cluster 10 of cluster domain 110*b* forms a protected space both in terms of network traffic and information access, incorporating a significant amount of redundancy, with a purpose to guarantee that cluster 10 is available at all times. Cluster 10 maintains a high degree of information integrity; implements secure ways of accessing information from clients external to the cluster, while meeting established security requirements associated with the connection of the medical devices of nodes 12 to outside equipment.

In one embodiment, if a medical device associated with a node 12 is for whatever reason accessed without using the node (e.g., via a virtual access discussed below), the medical device is subject to certain security requirements. For instance, if the medical device is to be connected, e.g., via a wired local area network ("LAN"), both to cluster 10 and to a piece of outside client equipment, then two separated LAN connectors are required in one embodiment, one connector reserved for cluster 10 connectivity and a second connector for open environment connectivity. In another embodiment, the LAN connectors may be shared for both the cluster and open environments but software isolation is employed. Separation within cluster 10 may therefore employ different combinations of hardware and software isolation between a cluster 10 LAN connection and the connection to the open environment. Providing such isolation and maintaining responsibility for quality, IT connectivity, and associated services inside a well confined cluster 10, where equipment is developed under a strict rigor associated with medical products, results in a redundant and highly stable system of operation.

One important application of cluster 10 is to support technical maintenance of the equipment occupying nodes 12. In the same way that nodes 12 replicate medical information, they may also replicate downloaded code (e.g., medical device software updates). By connecting, e.g., via a laptop or tablet device via an access node 12*a* or 12*h* (discussed below), a service technician may diagnose, configure and update software on the medical device, including the gathering of technical statistical information to promote preventive maintenance.

From a medical perspective, cluster 10 will assist in a multitude of areas, e.g., operational prescription management, treatment result assembly and storage, treatment session reporting, and medical record management and support. From an alarm perspective, cluster 10 constantly updates and distributes alarms and other real time events between nodes 12 of cluster 10, including medical equipment and access nodes 12.

Still another area in which cluster 10 may play an important role is for synchronization between different types of connected equipment. In one example, multiple online dialysis fluid generation dialysis machines may be connected fluidically to a central water supply loop that supplies purified water to the machines, which use the purified water to prepare dialysis fluid. The water supply loop needs to be cleaned periodically, e.g., via hot water disinfection. In an embodiment, the custom software of cluster 10 is able to ascertain when each of the dialysis machine nodes 12 is available for having its portion of the water supply loop disinfected, so that a disinfection sequence may be commenced that efficiently and optimally cleans the entire water supply loop, including portions of the loop connecting the machines to the remainder of the water supply loop. Cluster 10 may report out that all relevant medical device nodes 12 (non-medical device access nodes being excluded) are available for a cleaning session, upon which a central water plant initiates a hot water loop disinfection. Note that initiation of a request for disinfection of the central water supply loop may come from (i) within cluster 10, e.g., the proprietary software is programmed to prompt when all medical device nodes 12 are at rest and at least a certain amount of time or total service hours have passed since the last disinfection or (ii) the central water plant, e.g., after at least a certain amount of time or total service hours have passed since the last disinfection. Other examples of where the medical devices of nodes 12 may synchronize with outside equipment includes software updates, where an update may be scheduled for the next time each of the medical device nodes 12 is at rest, at which time cluster 10 reports out that it is ready for the new software.

It is also contemplated that the collaboration between nodes 12 of cluster 10 not be limited to medical applications. For example, cluster 10 may store and synchronize information to support patient in-center entertainment preferences, such as, favorite websites, television and radio channels, movies, food and beverages. This information is available no matter which medical device of cluster 10 is used to treat a patient.

The clusters 10 of cluster domain 110b offer a powerful platform having high integrity for a multitude of application areas listed below. The below list is not exhaustive, but serves to exemplify the variety of services that benefit from the closed cluster domain 110b. Each of the entries of the following list in one way another benefits from the safety, security and quality aspects that cluster domain 110b provides, including: (i) clinic administration services, (ii) staff and patient administration services, (iii) attention services including information presentation services, staff assistance call services, medical device alarm distribution services, and staff reminder services, (iv) connectivity services including cluster node connectivity services, connectivity level services, and dialysis monitor connectivity services, (v) equipment services including dialysis monitoring services, and water purification system services, (vi) financial services including dialysis billing services, (vii) identification services including dialysis session identification services, medication identification services, dialysis station identification services, disposable identification services, equipment identification services, patient identification services, and staff identification services, (viii) information management services including clinic information services, and patient information services, (ix) inventory services including inventory consumption tracking services, product traceability services, and reuse traceability services, (x) scheduling services including equipment scheduling services, patient scheduling services, and staff scheduling services, (xi) security services including access control services, availability protection services, confidentiality protection services, encryption services, and integrity protection services, (xii) therapy services including assessment services, consultation services, dialysis session services, dialysis session record services, medical tests services, prescription services, and vascular access services, and (xiii) water purification services including distribution loops services, and water quality services.

In FIG. 2, external domain 110a is in one embodiment an open IT environment domain using standard off-the-shelf hardware and software. The only exception to the off-the-shelf architecture being software applications deployed on external domain 110a equipment for the purpose of interacting with cluster domain 110b via interface domain 110c. In many instances, external domain 110a equipment is not readily programmable and therefore will not receive custom software for interfacing with cluster 10. Instead, access nodes 12a and 12h contain the interfacing software to read the data entering from the external equipment. In the case of a doctor's or clinician's computer, however, there may be application software that is installed on the computer that has counterpart application software stored at nodes 12 or software for interfacing with the application software stored at nodes 12. External domain 110a equipment may include non-proprietary devices that are not designed for inclusion cluster domain 110b and therefore need additional equipment (interface domain 110c) to exchange information with the cluster domain 110b.

FIG. 3 illustrates external domain 110a in more detail and operating with cluster domain 110b having access nodes 12a and 12h forming at least part of interface domain 110c. In the illustrated embodiment, external domain 110a is represented by the following classes or types of equipment: (i) external information systems 50a, which may be any information system external to cluster 10 that benefits from exchanging information with member nodes 12 of cluster 10, (ii) presentation equipment 50b, which may be any equipment primarily used for presenting information retrieved from cluster 10, e.g., display screens of all sizes and technologies (optionally of touch type), (iii) tablet and personal computer equipment 50c, which may be any keyboard- or touch-based user interface equipment used for exchanging information between external domain 110a and cluster domain 110c equipment, e.g., smartphones, smart pads, laptops, stationary personal computers ("PCs"), hybrids, and similar computer-based equipment, (iv) shared (e.g., medical) equipment 50d, which may be any equipment (medical or non-medical) used to support a medical device clinical process that is shared between patients as part of their pre- and/or post-registration activities during the presence at the clinic, e.g., patient pre/post treatment weight scale and registration stations, blood pressure stations, clinic arrival/departure registration and equipment deployed in the clinic for similar purposes (such shared equipment is normally equipped with, connected to and/or used with some kind of personal identification equipment), and (v) bedside (e.g., medical) equipment 50e, which may be any equipment (medical or non-medical) deployed at the patient's bedside and associated with (serving) a specific patient during part or full duration of treatment, e.g., water reverse osmosis units for dialysis fluid preparation, blood pressure meters, entertainment consoles and other equipment deployed at bedside for similar purposes.

While FIGS. 1 and 3 illustrate cluster 10 having both distributed database access node 12a and non-distributed database access node 12h, it should be appreciated that any cluster containing one or more nodes 12b-12g may have (i) one or more distributed database access node 12a only, (ii) one or more non-distributed database access node 12h only, (iii) one or more distributed database access node 12a and one or more non-distributed database access node 12h, (iv) a virtual access node 100 (described below) only, and (v) a virtual access node 100 in combination with any one or more of either or both distributed database access node 12a and non-distributed database access node 12h.

Figure 4:
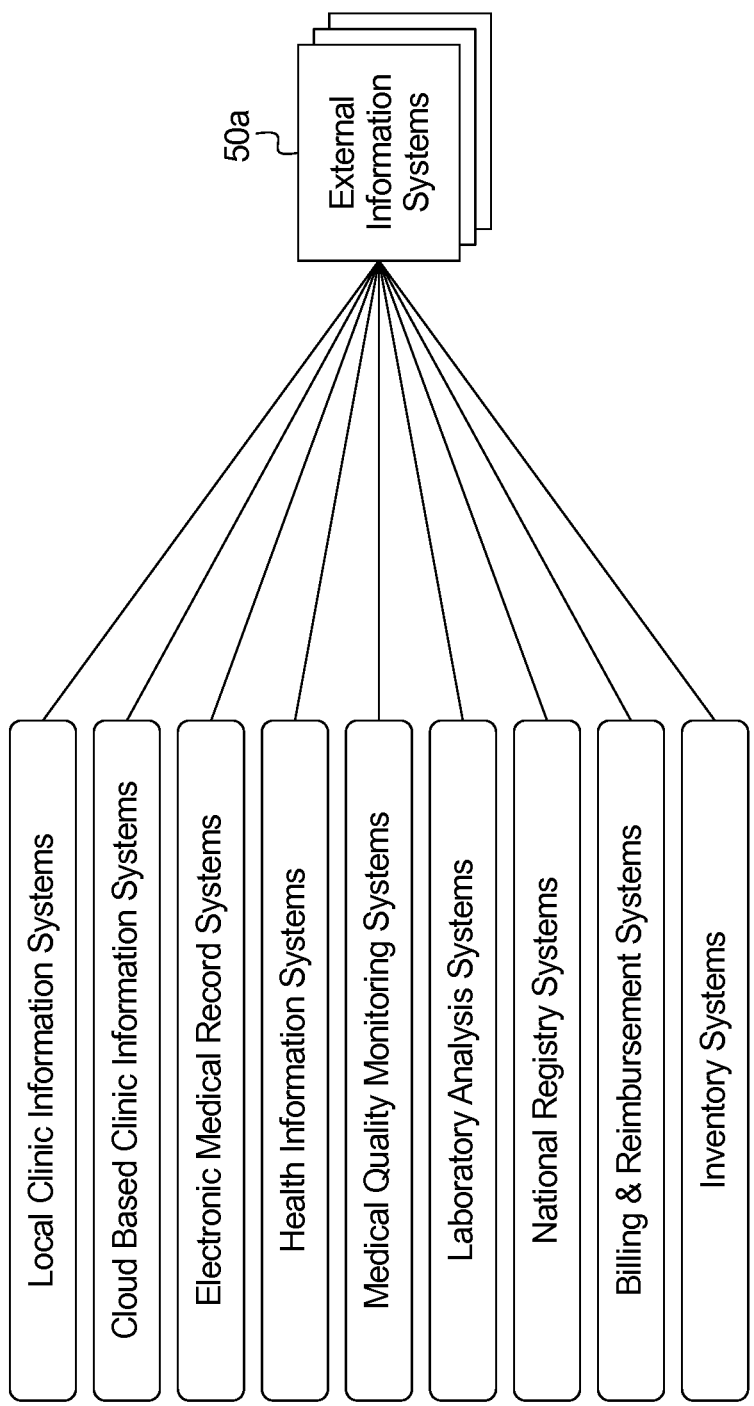
FIG. 4 is a schematic view further illustrating examples of external information system equipment.

FIG. 4 illustrates non-limiting examples of external information systems 50a. External information systems 50a may take many different forms from purely administrative ones, e.g., billing and reimbursement, to dedicated and specialized medically related systems, such as, laboratory analysis systems and clinic information systems. Examples listed in FIG. 4 include, but are not limited to, local clinic information systems, cloud based clinic information systems, electronic medical record systems, health information systems, medical quality monitoring systems, laboratory analysis systems, national registry systems, billing and reimbursement systems, and inventory systems.

External information systems 50a in an embodiment connect to cluster 10 via wired or wireless connection to one or more distributed database access node 12a of interface domain 110c.

Figure 5:
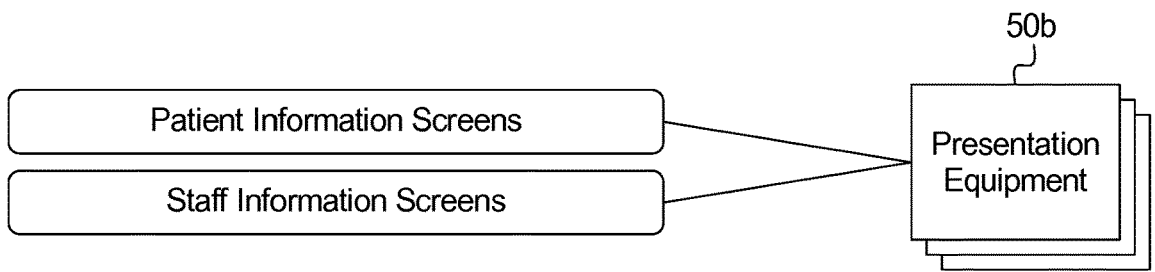
FIG. 5 is a schematic view further illustrating an example of presentation type external equipment.

FIG. 5 illustrates non-limiting examples of presentation equipment 50b. Presentation equipment 50b includes equipment, handheld or stationary (e.g. mounted on a wall), with a primary (but not exclusive) purpose of presenting information to staff and/or patients within a treatment clinic. Presentation equipment 50b in general does not generate data for input into the medical devices of cluster 10, however, they may optionally be used for input if, for example, they have touch support capability. Presentation equipment 50b may for example present patient information for guiding arriving patients through various steps during treatment. For example, the patient arriving at the clinic may have access to scheduling information including pre-post weight registration location/status and treatment station location for receiving treatment. Staff information screens may present patient preparation status, dialysis station occupancy and treatment progress, and alarm information for various treatment locations in the clinic.

Presentation equipment 50b in an embodiment connects to cluster 10 via wired or wireless connection to one or more distributed database access node 12a of interface domain 110c.

Figure 6:
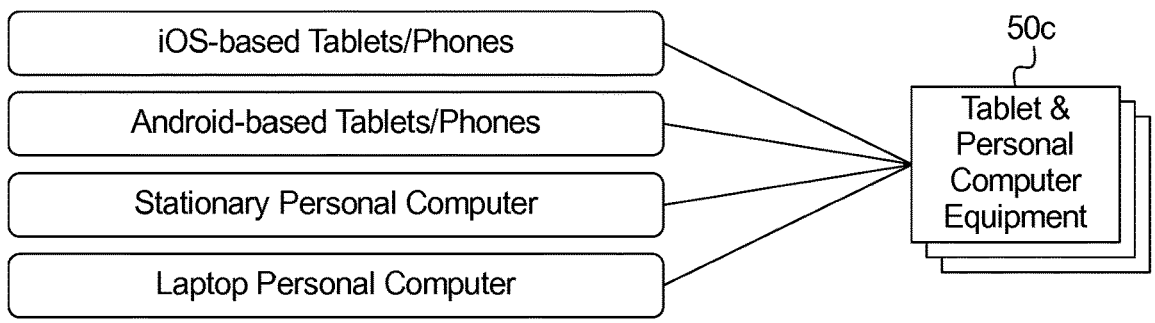
FIG. 6 is a schematic view further illustrating an example of tablet and computer type external equipment.

FIG. 6 illustrates non-limiting examples of tablet and personal computer ("PC") equipment 50c. Tablet and PC equipment 50c may require more input intensive and advanced information exchange that what is at presently practical using handheld, e.g., smartphone or tablet, devices. However, the advancement of tablets and of hybrid tablet/PC technology brings both types of devices under equipment 50c. Software deployed on equipment 50c may range from very simple applications to highly advanced applications including a complete CIS interface and environment towards accessing the information stored within cluster 10. Such applications may present a user interface for clinic staff (physicians, nurses, technical service staff, and administrative staff, etc.) to access and update information or feature in service areas, such as, administration services, staff and patient attention services, connectivity services, equipment technical service and maintenance services, billing and reimbursement services, identification services, information management services, inventory services, scheduling services, security services, patient medication services, therapy services and water purification services.

Tablet and PC equipment 50c in an embodiment connects to cluster 10 via (i) wired or wireless connection to one or more distributed database access node 12a of interface domain 110c or (ii) virtual access connection without access node hardware. Mobile connections enable a physician to make bedside changes to the original operating parameter prescriptions, changes that are then immediately distributed into shared data 14 and that take effect at the appropriate medical device of a node 12. A laptop or stationary PC may be used alternatively where mobility is not a top priority, e.g., for longer sessions interacting with cluster 10.

Figure 7:
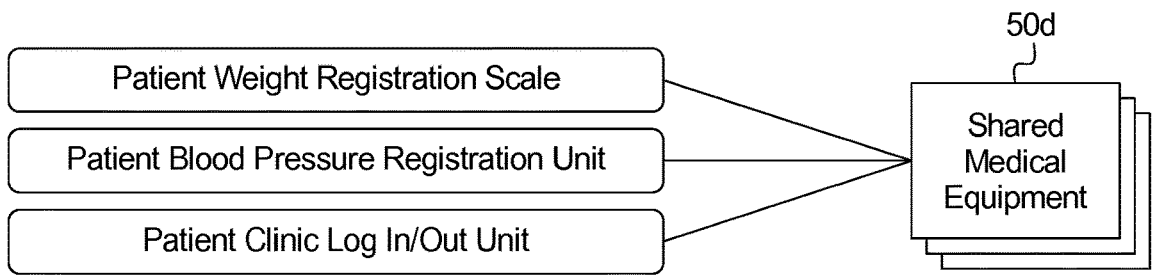
FIG. 7 is a schematic view further illustrating an example of shared medical type external equipment.

FIG. 7 illustrates non-limiting examples of shared, e.g., medical, equipment 50d. Shared, e.g., medical, equipment 50d includes equipment shared between patients present at the same time in a clinic. Shared equipment 50d may have medical or non-medical purposes. Although equipment for shared medical or medically related purposes is prevalent, a variety of other equipment, such as equipment that serves administrative purposes and/or supports the clinical therapy process, also falls under this category.

One example is patient weight pre-treatment and post-treatment registration. A weight scale may be shared by multiple patients in a clinic or other treatment setting. Each patient is identified at the time of weighing, e.g., by entering the patient's name or patient identification ("ID") into the weighing equipment or via, e.g., a patient ID card presented to equipment present at the weighing station. The registered and identified weight is then transferred to distributed database 14 of cluster 10 and stored for example in a weight file for that patient. The medical device of whichever node 12 that the patient is assigned to retrieves the patient's pre-treatment weight for that day and for example enters the weight into the machine for use with the patient's prescription. Pre-treatment weight may be used in combination with a known dry weight to determine how much excess blood water or ultrafiltration to remove from the patient undergoing a dialysis treatment. Other examples of shared equipment include blood pressure measurement equipment, glucose measuring equipment, and patient log-in and log-out equipment for registration when the patient enters and leaves the clinic.

Shared equipment 50d in various embodiments connects to cluster 10 via wired or wireless connection to one or more distributed database access node 12a or non-distributed database node 12h of interface domain 110c. Non-distributed database access node 12h may be used if the shared equipment 50d has no need for any data from distributed database 14.

Figure 8:
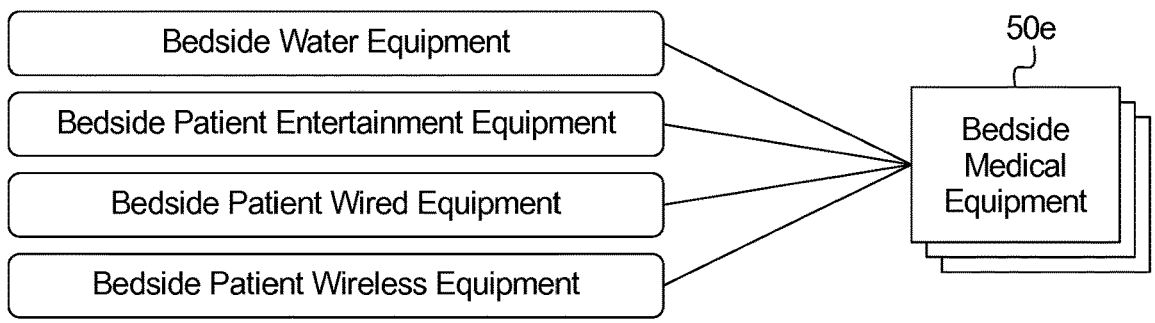
FIG. 8 is a schematic view further illustrating an example of bedside medical type external equipment.

FIG. 8 illustrates non-limiting examples of bedside, e.g., medical, equipment 50e. Bedside equipment may, just like shared equipment 50d, have a medical or non-medical reason or purpose. Non-medical bedside or patient-dedicated equipment 50e may include, for example, personal communication, entertainment (e.g., HDMI connected televisions), patient work-related equipment, and patient identification equipment. Non-medical bedside or patient-dedicated equipment 50e may not need access to data from distributed database 14 and if so may connect to cluster 10 via wired or wireless connection to one or more non-distributed database node 12h of interface domain 110c. Shared data 14 may however benefit from interacting with non-medical bedside equipment 50e. In an example, distributed database 14 of cluster 10 may form a personal preferences file for each patient storing individual preferences with respect to favorite websites, television channels, radio stations, etc.

Bedside or patient-dedicated equipment 50e may of course be medical related. Certain clinics may provide blood pressure cuffs for each medical device of a node 12, so that blood pressure may be tracked during treatment. Another example is water purification equipment used to make dialysis fluid for dialysis. In either case, medical bedside or patient-dedicated equipment 50e may or may not need access to shared data 14 and therefore connect to cluster 10 via (i) wired or wireless connection to one or more distributed database access node 12a or one or more non-distributed database node 12h of interface domain 110c or (ii) a virtual access node as described herein.

Another example involves the delivery of drugs to the patient during a hemodialysis or other blood cleansing treatment, e.g., Epogen™ for red blood cells or Venofer™ for iron/sucrose. These drugs may be delivered by a dialysis machine pump of a node 12 or via an external pump. If provided by a dialysis machine pump, then drug delivery is already part of cluster 10. If by a separate pump, however, which for example is a floating pump used in the clinic as needed, the separate pump may access distributed database 14 via distributed database access node 12a or non-distributed database node 12h of interface domain 110c for two-way communication between the drug delivery pump and the dialysis machine of node 12. Dialysis machine of node 12 adds any desired drug delivery data to distributed database 14 of cluster 10, while the external drug delivery pump may record any desired data, such as patient response after delivery in the form of a blood pressure reading, a bioimpedance reading, hydration level reading, or a subjective response from the patient entered into the user interface of the dialysis machine. The drug delivery pump in an embodiment is part of its own cluster 10 of floating pumps and feeds data to its own distributed database 14.

A further example involves a hospital room or drug delivery setting in which a patient is receiving multiple drugs. Here, it is contemplated to implement one or more cluster 10. A first cluster 10 may be formed around the patient, where nodes 12 are formed by the different pumps or different channels of one or more pump along with any equipment analyzing the patient during drug delivery. The resulting distributed database 14 may be used for electronic medical records ("EMR"), billing and other purposes, and proprietary software may be written to achieve any goal for the shared data 14. For example, it may be desirable to (i) record any reactions to a delivered drug, e.g., blood pressure reading, a bioimpedance reading, hydration level reading, or a subjective response from the patient entered by a nurse or (ii) record any reactions to a combination of delivered drugs, e.g., blood pressure reading, a bioimpedance reading, hydration level reading, or a subjective response from the patient entered by a nurse. Time of drug delivery, dose, dose rate, etc., may also bee recorded for each drug.

A second cluster 10 may be formed around a particular drug where, for example, a drug manufacturer may find collective data concerning its drug to be very valuable. Here, nodes 12 reside at multiple bedsides, each delivering the drug to be analyzed. Proprietary software may be written to strip or simply not record any patient identification data but to record, for multiple patients, any reactions to the delivered drug, e.g., blood pressure reading, a bioimpedance reading, hydration level reading, or a subjective response from the patient entered by a nurse into distributed database 14. The proprietary software may be written to record patient type data, e.g., sex, age, race, ethnicity at distributed database 14. The software may also record data gleaned from the delivery of other drugs, e.g., any of the above reactions while the patient is receiving the manufacturer's drug in combination with one or more other drugs in distributed database 14. Here, such other drug information may come in through one or more access node 12a or 12h.

As noted above, both drug delivery clusters 10 just described may be run concurrently and simultaneously.

Figure 9:
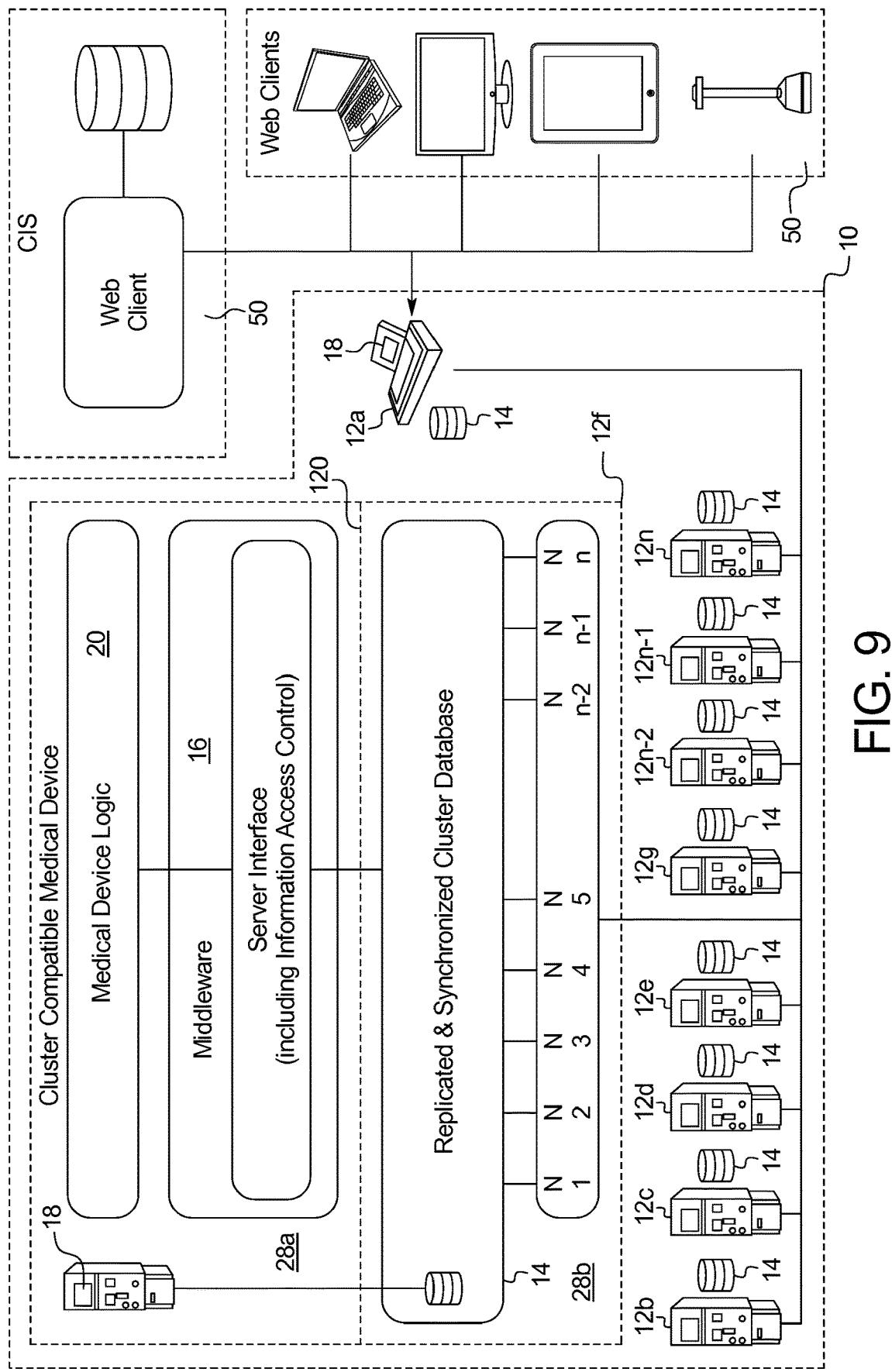
FIG. 9 is a schematic view illustrating one embodiment of a distributed database access node and an enlarged view of a medical device node of the cluster system of the present disclosure.

Referring now to FIGS. 2, 3 and 9, interface domain 110c is described in more detail. Cluster interface domain 110c acts as a façade to access the services of the cluster configuration without exposure of the internals of the actual cluster implementation, infrastructure and setup. As discussed above, access nodes 12a and 12h form part of interface domain 110c. Also discussed above, most of equipment 50a to 50e (referred to herein collectively as equipment 50 or generally individually as equipment 50) may be connected to distributed database via a distributed database access node 12a, a non-distributed database node 12h, or a virtual access node if the primary purpose of the access is information access only.

In an embodiment, distributed database access node 12a is a full-fledged member of cluster 10 and holds a replicated set of data 14 identical, in terms of content as well as service capabilities, to distributed database 14 hosted by medical equipment nodes 12b to 12g in FIGS. 1, 2, and 9. Cluster 10 via access nodes 12a and 12h will therefore still be available for external access even if all other medical device nodes 12b to 12g of cluster 10 are switched off. In an embodiment, non-distributed database node 12h provides an interface conversion between equipment 50 of external domain 110a (e.g., arbitrary equipment not meeting cluster 10 infrastructure requirements) and internal (protected) infrastructure of cluster domain 110b. Non-distributed database node 12h for example allows data from arbitrary shared equipment 50d and bedside equipment 50e along with patient identify data from a patient identity device to be sent to distributed database 14 for patient medical record storage.

In terms of connectivity capabilities, distributed database access node 12a and non-distributed database node 12h are identical in one embodiment. Each may connect to any of the above-described types of equipment 50a to 50e.

FIG. 2 illustrates that interface domain 110c includes a third type of access into distributed database 14 of domain 110b, namely, a virtual access node 100. Virtual access node 100 is virtual because there is no additional equipment representing a node, as is the case for access nodes 12a and 12h. Virtual access node 100 in an embodiment requires that responsibility for maintaining isolation between external domain 110a and cluster domain 110b be shared between the connected client equipment 50 and medical device nodes 12 of cluster 10. Client equipment 50 is in one embodiment connected to cluster domain 110b in such a way to guarantee the integrity of the information transferred to cluster 10. Secure connectivity may be provided via a virtual private network ("VPN") connection made directly to the cluster 10 environment. Virtual access node 100 may for example allow a doctor, clinician, or technician computer that is connected within the clinic or medical device setting via a VPN to access distributed database 14. Such computers may run device prescription software that develops operational routines for the medical devices of nodes 12. The computers via virtual access node 100 may operate to send and receive lab results, for example, to be entered into the prescription software. Once the prescription operation routine is completed, it may be deposited via virtual access node 100 onto distributed database 14 under a folder for the patient or patients for which the operational routine has been developed. Client computers may also use the protected virtual access node 100 to pull data from distributed database 14 of cluster 10, e.g., to review treatment results from one or more operational routine to see if it needs to be modified or replaced.

Figure 10:
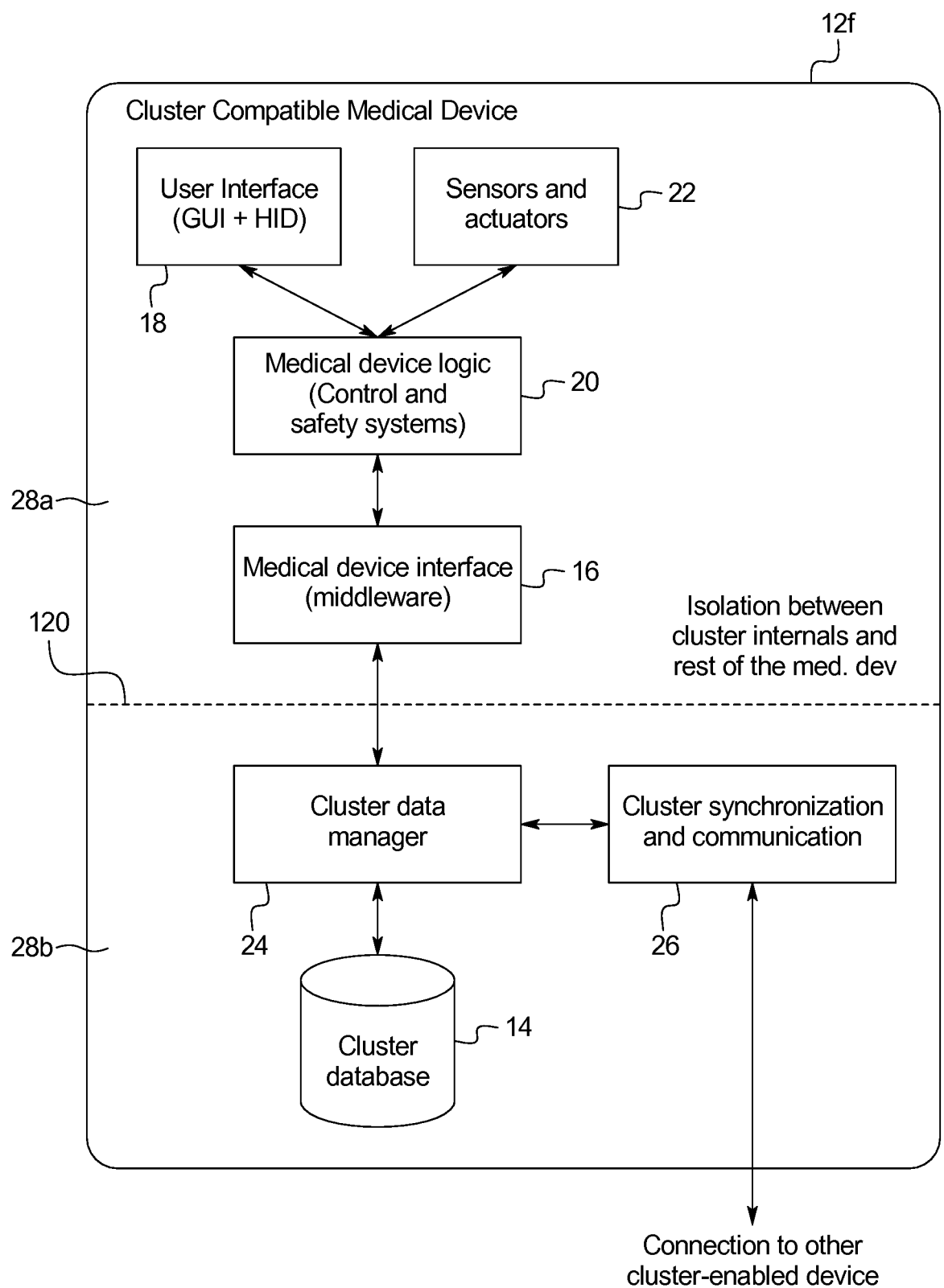
FIG. 10 is a schematic view further illustrating the isolation aspects of a medical device node of the cluster system of the present disclosure.

Referring now to FIGS. 9 and 10, cluster compatible medical device nodes 12b to 12g . . . 12n are illustrated in more detail. FIG. 9 illustrates medical device nodes 12b to 12g . . . 12n operating within cluster 10 and highlights medical device node 12f, while FIG. 10 provides more detail on the distributed database 14 side of medical device node 12*f*. FIGS. 9 and 10 both illustrate that medical device node 12*f* includes two separate (separated by hardware and/or software) parts, namely, a therapy control part 28*a* and a cluster control part 28*b*. Therapy control part 28*a* in the illustrated embodiment includes a server interface hosted on middleware 16. Server interface and middleware 16 operates with medical device operating software 20, which may include any one or more of a main medical device control processor and memory, one or more safety processor and memory, a user interface processor and memory and one or more lower level controllers, such as, sensor boards, pump control boards, etc., for sensors and actuators 22 (FIG. 10). Any and all of the above functions may be combined alternatively on a single processor and memory.

Server interface and middleware 16 in the illustrated embodiment drives user interface 18 of medical device nodes 12. User interface 18 may, for example, display set-up screens, treatment screens, technical data, etc. If the patient wishes to view web pages from websites desired by the patient, e.g., via an internet connection provided by the hospital or clinic, the patient may do so at a user interface 18 of an access node, such as distributed database access node 12*a*, provided as part of cluster 14 in FIG. 9. Such websites may be stored in a preferences file for the patient in distributed database 14, so that the preferred website is known regardless of which access node of cluster 10 the patient uses next. An access node 12*a*, 12*h* may be placed at each medical device node 12*b* to 12*g* . . . 12*n* to provide internet access for use by the patient and/or caregiver.

Cluster control part 28*b* houses replicated database 14, which in FIG. 9 is shared by medical devices at nodes 12*a* to 12*g* and 12*n*-2 to 12*n* of cluster 10. Cluster control part 28*b* is structured carefully to meet requirements for security, safety, availability, integrity and others for the protected internal cluster infrastructure. Additionally, because therapy control part 28*a* runs treatments, it is responsible for the patient's safety and therefore should not face competition over resources (clock cycles, memory consumption, etc.) with distributed database 14. In an embodiment a processing and memory manager 120 may therefore be applied between therapy control part 28*a* and cluster control part 28*b* of medical device node 12*f*. Processing and memory manager 120 may for example be supported by a Linux™ operating system or other operating system capable of handling hardware-supported processing and memory protection and virtualization. Processing and memory manager 120 in an embodiment copies (i) data originating from the therapy control part 28*a* into cluster control part 28*b* and (ii) data that originates from cluster control part 28*b* into therapy control part 28*a*, in a way that preserves isolation between parts 28*a* and 28*b* (e.g., parts 28*a* and 28*b* never share or see each other's memory areas).

In one embodiment, server interface and middleware 16 of therapy control part 28*a* knows when it is free to share data with distributed database 14 and is therefore given the responsibility of initiating a data transfer with internal part 112*b*. Server interface and middleware 16 of therapy control part 28*a* sends data to cluster control part 28*b* via memory processing and memory manager 120 when it has data to send and opens itself to receiving data from distributed database 14 when it is ready.

FIG. 10 illustrates cluster control part 28*b* in more detail. Besides distributed database 14, cluster control part 28*b* includes a cluster database manager 24 and a cluster communication interface 26. Cluster database manager 24 and cluster communication interface 26 may be separate pieces of software, in which cluster database manager 24 is responsible for receiving data from middleware software 16 via processing and memory manager 120 and securely converting the data into a storage format suitable for distributed database 14. Cluster database manager 24 is also responsible for securely converting data retrieved from distributed database 14 into a form suitable for middleware software 16 and medical device operating software 20 of therapy control part 28*a*.

Cluster communication interface 26 in an embodiment is a messaging supervisor for controlling how data is to be sent to and received from other nodes 12 of cluster 10. Discussed above are many different ways that data may be distributed between the different nodes 12 of cluster 10. Cluster communication interface 26 knows the selected data transport configuration and causes its node 12*f* to send and/or receive data, securely and completely, at the appropriate time and/or in the appropriate order with other nodes 12.

Figure 11:
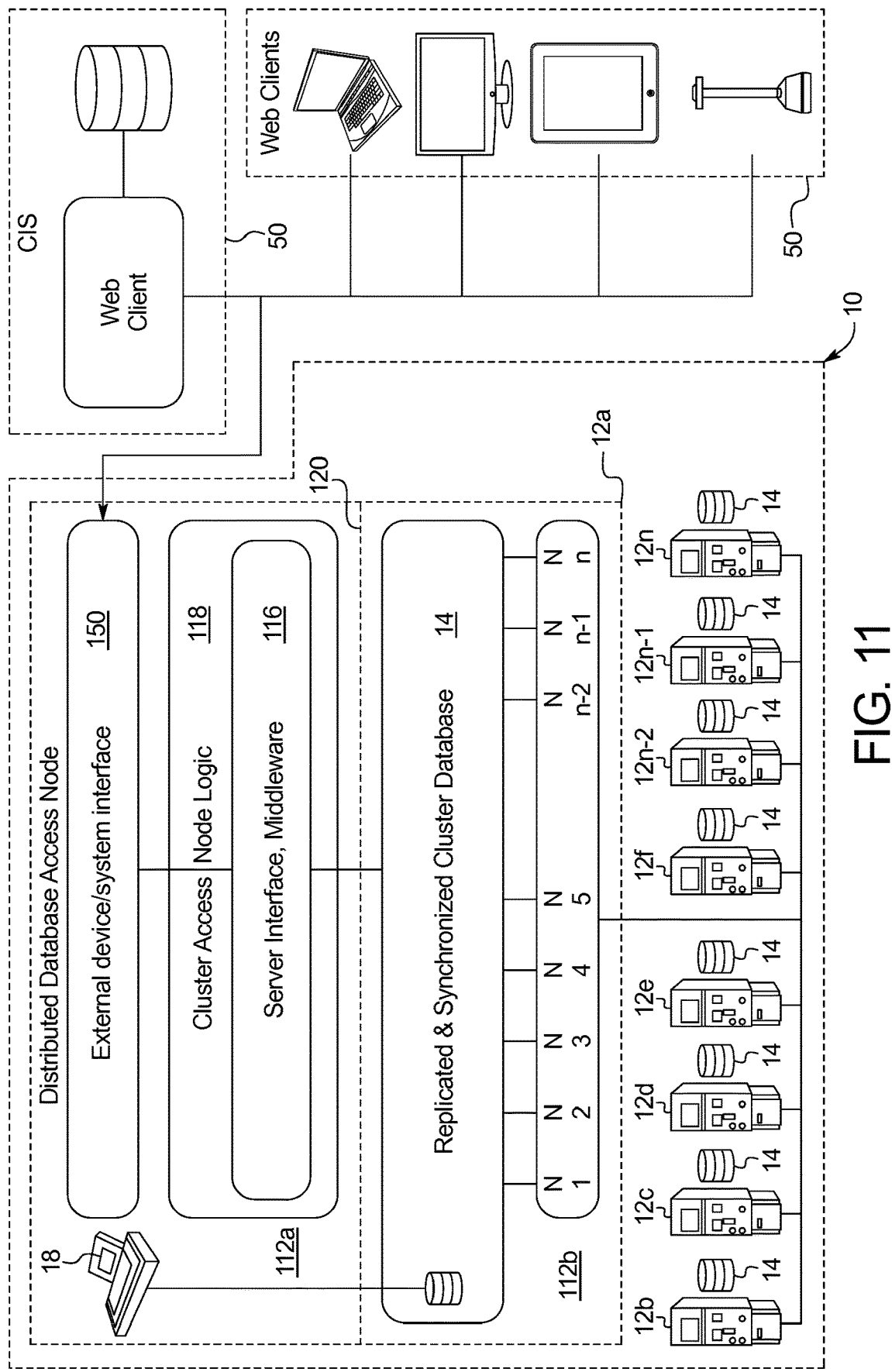
FIGS. 11 and 12 are schematic views illustrating one embodiment of an enlarged view of a distributed database access node of the cluster system of the present disclosure.
Figure 12:
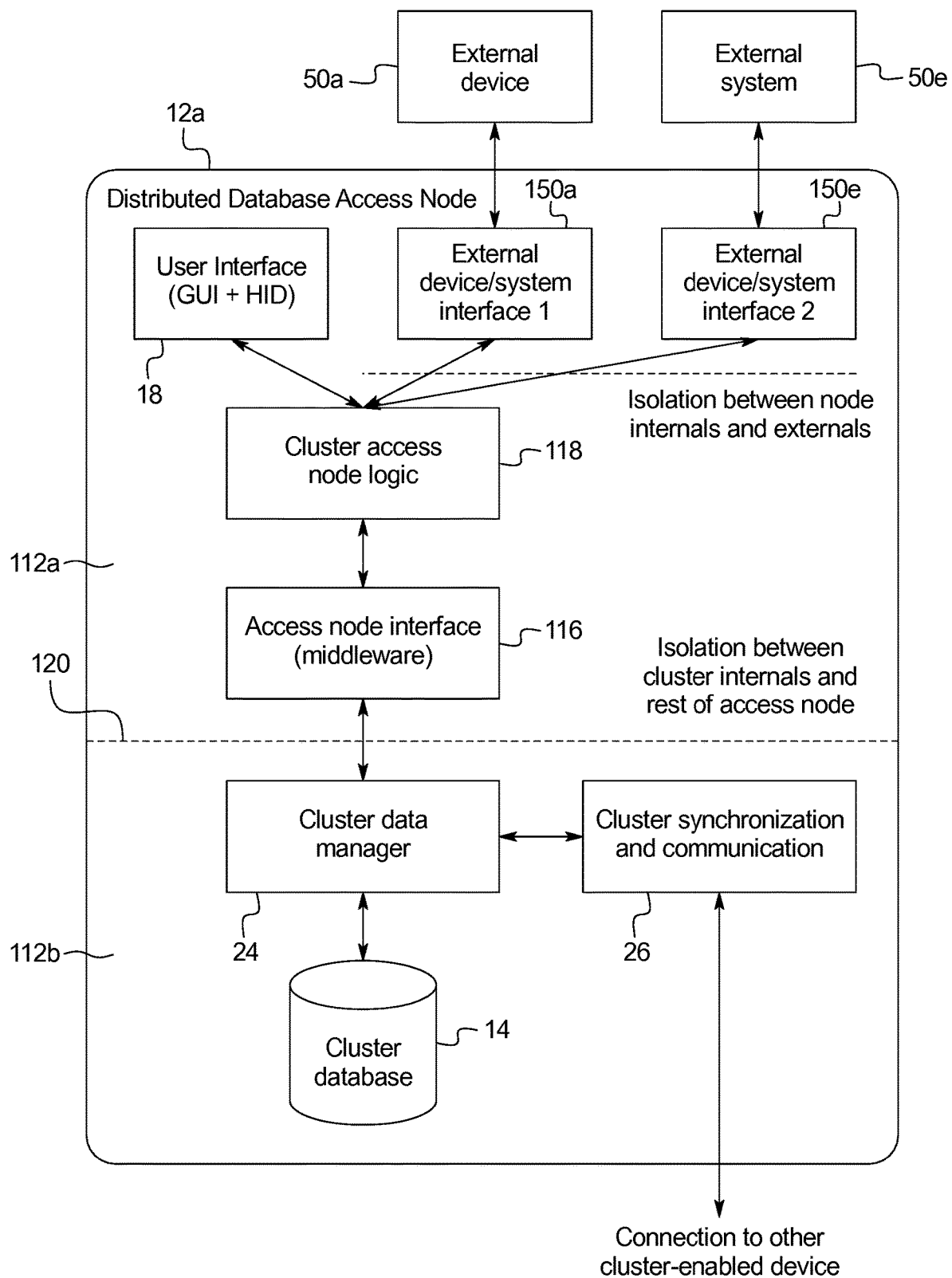

Referring now to FIGS. 11 and 12, distributed database access node 12*a* is illustrated in more detail. Distributed database node 12*a* includes and is part of distributed database 14 and interacts with external equipment 50 as has been discussed herein. Distributed database node 12*a* includes its own server interface and middleware 116 hosted operating with cluster access node logic 118 (operating software for the access node). Distributed database access node 12*a*, similar to medical device nodes 12*b* to 12*g* and 12*n*-2 to 12*n*, includes an external part 112*a* and an internal part 112*b* separated by processing and memory manager 120 as described above, so that a clear and distinct separation between distributed database 14 and server interface and middleware 116 is established. Distributed database access node 12*a* is able to retrieve and send information from distributed database 14 to external equipment 50. Distributed database access node 12*a* may receive and store in shared distributed database 14 data from external equipment 50, such as the CIS, and server clients such as a computer, a display device, a handheld smart device, such as a smartphone or smart tablet, and/or medical equipment, such as a weight scale.

Connectivity between external part 112*a* and external equipment 50 may for example be via wired local area network ("LAN"), wireless local area network ("WLAN"), or Bluetooth technology, etc. If connection is made via a physical LAN cable between external equipment 50 and distributed database access node 12*a*, the cable may be a separate cable from any other external equipment cable and be connected to a dedicated port of the access node 12*a*.

FIGS. 11 and 12 illustrate that distributed database access node 12*a* may include its own user interface 18, which operates with server interface and middleware 116. As discussed above, user interface 18 of distributed database access node 12*a* may display internet sites to a patient undergoing treatment or to a caregiver, e.g., needing assistance. User interface 18 may also display set-up screens, treatment screens, technical data, etc., to the patient or caregiver. Again, the selection of any external content by the patient or caregiver may be stored in a preferences file in shared database 14.

Data transfer between external equipment 50 and distributed database 14 may occur without application interference directly via cluster access node logic 118. Access node interface and middleware 116 and access node logic 118 may host access node configuration software and applications, e.g., web clients (internet explorer, google chrome, etc.), for user interaction via a user interface 18 integrated or externally connected to access node 12*a*. Cluster access node logic 118 may error check the data and if needed combine data into a form useable with distributed database 14. For example, there may be a first external equipment 50 that provides a treatment operating prescription to distributed database access node 12a and a second external equipment 50 that provides patient weight data. Cluster access node logic 118 may assist in sorting and assembling related data, e.g., data associated with a same patient ID, and route the to a particular entry in distributed database 14.

FIGS. 11 and 12 further illustrate that distributed database access node 12a may however store different external device/system interface software, e.g., software 150a and 150e (referred to herein collectively as external device/system interface software 150 or generally individually as external device/system interface software 150) for different external equipment, e.g., 50a and 50e, respectively. External device/system interface software 150 is provided for certain external equipment 50 to send and receive information to and from distributed database 14. The interplay between external device/system interface software 150 and cluster access node logic 118 provides a first layer of isolation (as indicated by upper dotted line in external part 112a in FIG. 12). The purpose of this first isolation is to prevent erroneous or malicious external devices from affecting access node logic 118.

Internal part 112b, separated by processing and memory manager 120 from external part 112a, of distributed database access node 12a operates in the same manner as cluster control part 28b described above for medical device node 12f. In particular, database manager 24 may be responsible for receiving data from cluster access node logic 118 via processing and memory manager 120 and securely converting the data into a form suitable for distributed database 14. Cluster communication interface 26 is again a messaging supervisor for knowing how data is to be sent to and received from different nodes 12 of cluster 10. Processing and memory manager 120 provides a second layer of isolation to distributed database access node 12a.

Figure 13:
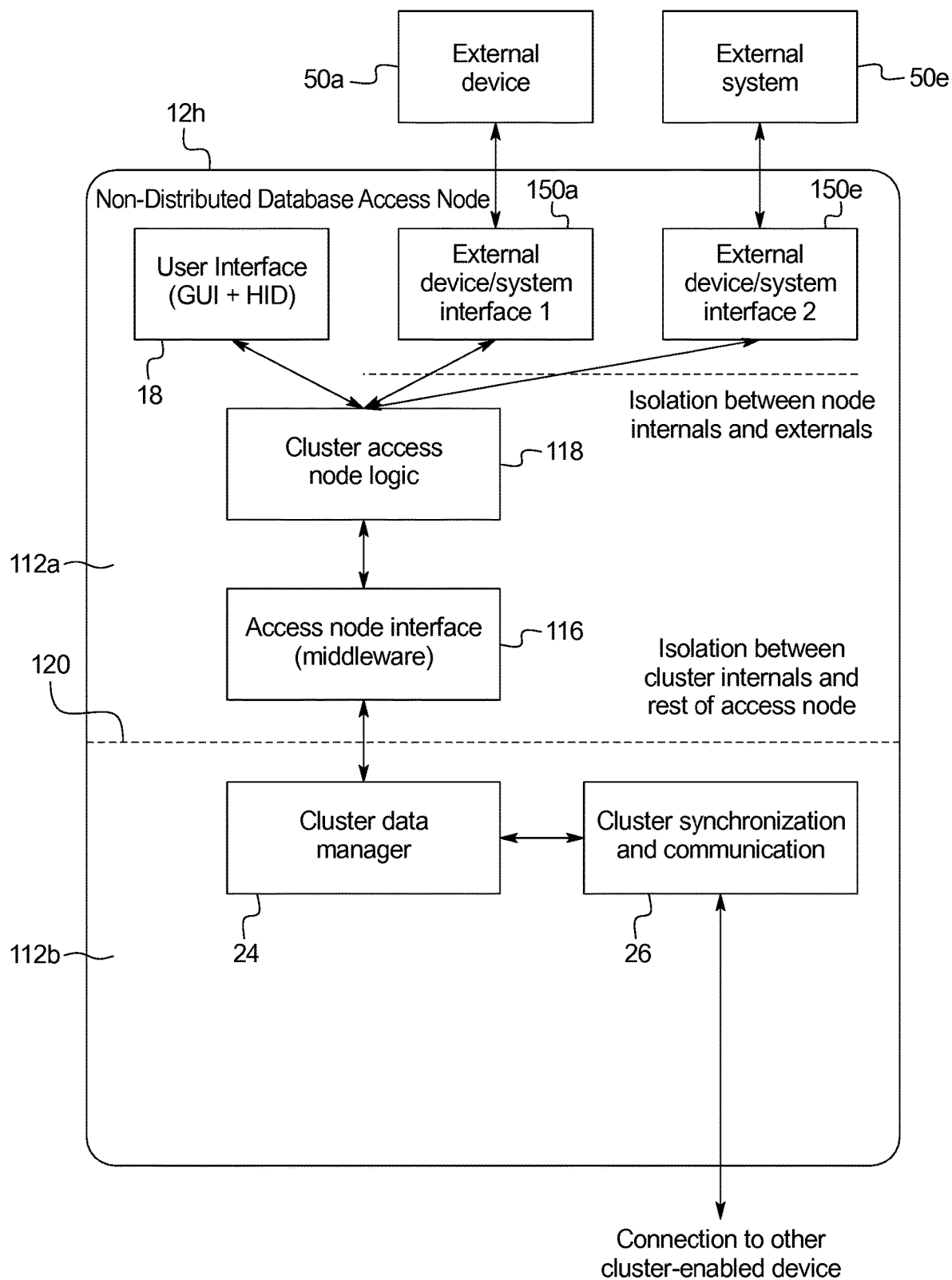
FIG. 13 is schematic view illustrating one embodiment of an enlarged view of a non-distributed database access node of the cluster system of the present disclosure.

Referring now to FIG. 13, non-distributed database access node 12h is illustrated in more detail. Non-distributed database node 12h does not have its own memory storage for distributed database 14 but does interact with external equipment 50 as has been discussed herein. Non-distributed database node 12h may send and receive data to and from distributed database 14, respectively, and data from distributed database 14 may be displayed on its user interface 18. But distributed database 14 is not resident at non-distributed database node 12h and therefore may not be accessed without access to other nodes. With distributed database access node 12a, on the other hand, database 14 is accessible even if access node 12a is the only available node 12 of cluster 10.

External device/system interface software 150, server interface and middleware 116, cluster access node logic 118, processing and memory manager 120, database manager 24 and cluster communication interface 26 of non-distributed database access node 12h operate the same in one embodiment as described or referenced above for distributed database access node 12a.

In the above embodiments, therapy control part 28a/external part 112a may be provided on its own one or more processor and memory separate from one or more processor and memory used for cluster control part 28b/internal part 112b. In an alternative embodiment therapy control part 28a/external part 112a may be provided on the same processor and memory as cluster control part 28b/internal part 112b, but be maintained on different parts of the memory and still be separated by processing and memory manager 120.

Moreover, while access nodes 12a and 12h have been described as being physically separate from medical device nodes 12b to 12g and 12n-2 to 12n of cluster 10, the additional structure and functionality of access nodes 12a and 12h may be provided alternatively as a separate node housed in a common housing with one of the medical device nodes 12b to 12g and 12n-2 to 12n. In particular, server interface and middleware 116, cluster access node logic 118, and external device/system interface 150 may be added as an external part 112a, as described above, that operates alongside the therapy control part 28a of medical device node 12b to 12g and 12n-2 to 12n. In an embodiment, both control part 28a and external part 112a are separated from cluster database 14, cluster database manager 24 and cluster communications interface 26 via processing and memory manager 120 in the manner described herein. The access node 12a within the medical device is a separate node from the medical device node 12b to 12g and 12n-2 to 12n in one embodiment. It operates independent of the medical device node even though the two nodes share the same housing and may share cluster database manager 24 and cluster communications interface 26. Information received by the access node 12a is not necessarily intended for its host medical device and may be information needed by another medical device of cluster 10. The information is stored on distributed database 14. Likewise, access node 12a located within the medical device may pull data from distributed database 14 and send it to outside equipment 50 regardless of whether the information has been generated by the host medical device or another medical device of cluster 10.

Figure 14:
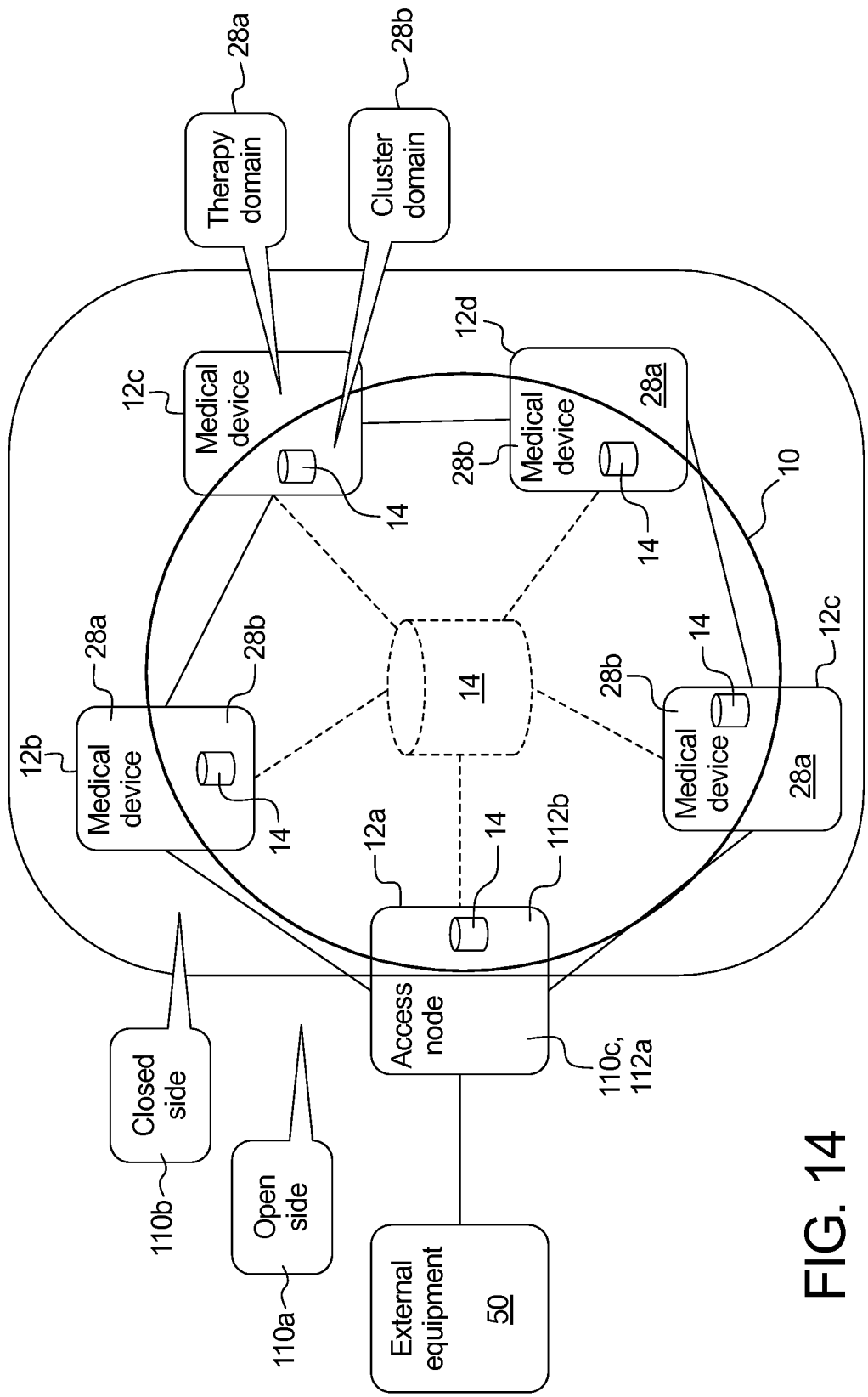
FIG. 14 is a schematic view illustrating one embodiment of how the cluster domain includes the cluster having the distributed database and a therapy control part of each medical device node.

Referring now to FIG. 14, the therapy control part 28a and cluster control part 28b of medical device nodes 12b to 12e and the external part 112a and internal part 112b of distributed database access node 12a of FIGS. 9 to 13 are illustrated together with the external domain 110a, cluster domain 110b, and interface domain 110c of FIG. 2. FIG. 14 represents cluster 10 via a circle and shows that cluster domain 110b includes cluster 10. Additionally, cluster domain 110b includes therapy control parts 28a of medical device nodes 12b to 12e. FIG. 14 reiterates that external domain 110a includes external equipment 50.

FIG. 14 also illustrates that cluster 10 includes cluster control parts 28b of medical device nodes 12b to 12e and internal part 112b (including distributed database 14) of distributed database access node 12a (would also include internal part 112b of non-distributed database access node 12h). External part of distributed database access node 12a in the illustrated embodiment is not part of cluster domain 110b and instead forms interface domain 110c along with the external parts 112a of any other access nodes of cluster 10. FIGS. 2 and 3 illustrate distributed database access node 12a having distributed database 14 within interface domain 110c. Distributed database 14 is shown this way in FIGS. 2 and 3 to differentiate distributed database access node 12a from non-distributed database access node 12h. It should be appreciated from FIG. 14, however, that distributed database 14 of full access node 12a belongs within cluster 10 of cluster domain 110b.

Figure 15:
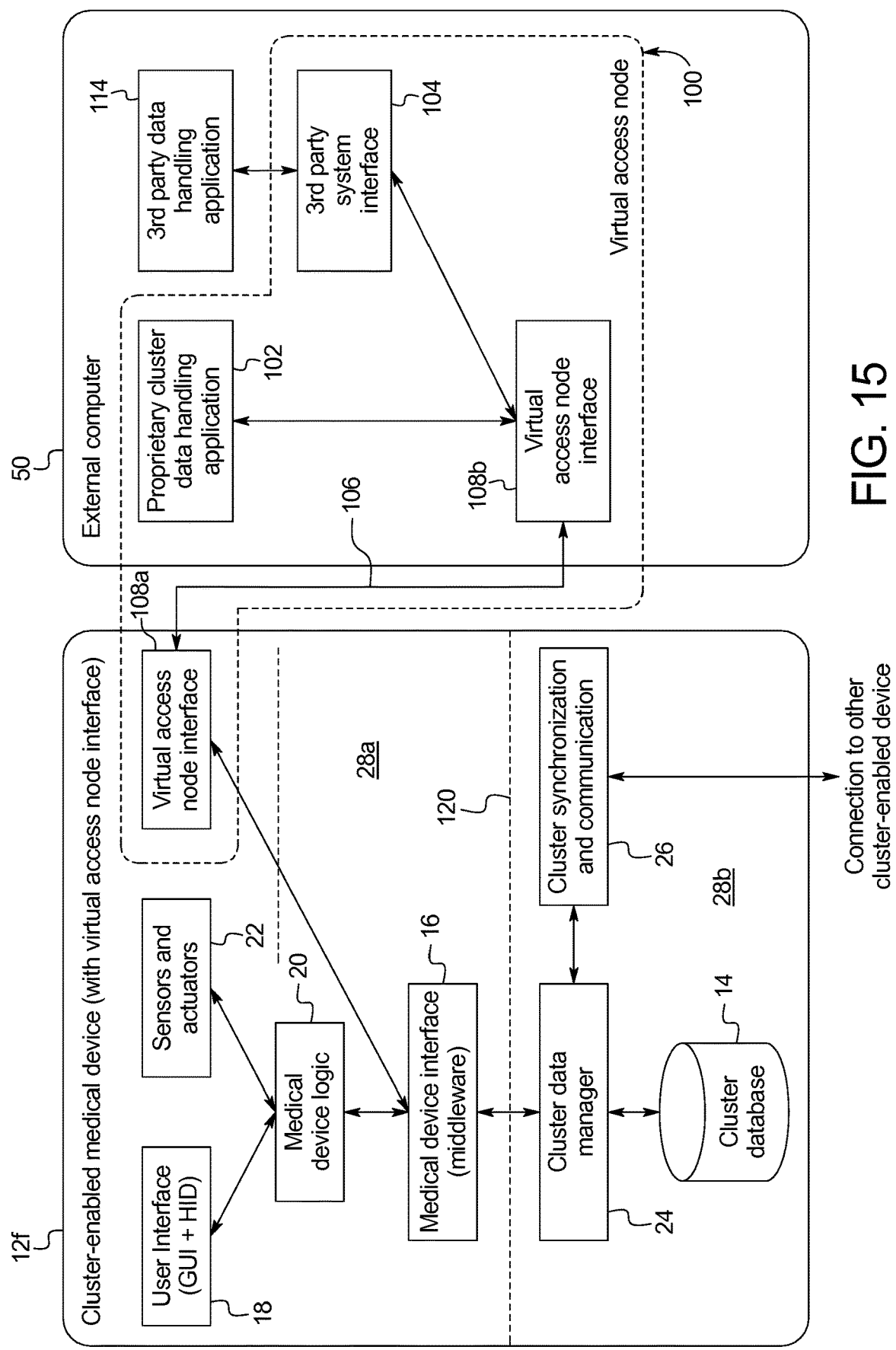
FIG. 15 is a schematic view illustrating one embodiment of a virtual access node of the cluster system of the present disclosure.

Referring now to FIG. 15, one embodiment for virtual access node 100 is illustrated. Virtual access node 100 in the illustrated embodiment includes an interface between a medical device node, such as medical device node 12f and a piece of external (open side) equipment 50, such as an external computer (doctor, nurse or technician computer).

Medical device node 12*f* is provided with each of the structures and associated functionality described above in connection with FIG. 10 for middleware 16, user interface 18, server interface 20, actuators 22, distributed database 14, cluster database manager 24, and cluster communications interface.

Computer 50 in the illustrated embodiment has installed thereon third party application software 114, such as software for developing treatment operating prescriptions. Third party application software 114 may for example receive data from distributed database 14 and use it to analyze or form new treatment operating prescriptions. If the desired third party application software 114 does not exist or the hospital or clinic does not own such software, it is contemplated to provide virtual access node 100 with proprietary data handling software 102 that performs the same and/or additional functions as third party application software 114 using the data retrieved from distributed database 14. In either case, proprietary data handling software 102 and third party application software 114 may in turn create data that is stored at distributed database 14.

A third party system interface 104 converts data from third party application software 114 into a form required by a secure communication channel, e.g., a virtual private network ("VPN") 106, present between medical device virtual access node interface 108*a* and an external equipment virtual access node interface 108*b*. VPN 106 is in essence an encrypted bridge between medical device node 12*f* and external equipment 50. VPN 106 may be provided and installed by the installer of cluster 10. Proprietary data handling software 102 in the illustrated embodiment, after conversions performed by third party system interface 104, is structured to communicate directly over VPN 106 between medical device virtual access node interface 108*a* and an external equipment virtual access node interface 108*b*.

Once inside medical device node 12*f*, data from external equipment virtual access node interface 108*b* is sent securely from therapy control part 28*a* to cluster control part 28*b* via processing and memory manager 120, is made available to distributed database 14 via cluster database manager 24, and is sent to other nodes via cluster communications interface 26 in a manner described above. Data from distributed database 14 may be converted via cluster database manager 24 and be sent securely from cluster control part 28*b* to therapy control part 28*a* via processing and memory manager 120, sent from interface 108*a* to interface 108*b* over VPN 106 and from there to one or both proprietary data handling software 102 and/or third party application software 114 via conversion at third party system interface 104.

It should be understood that various changes and modifications to the presently preferred embodiments described herein will be apparent to those skilled in the art. Such changes and modifications may be made without departing from the spirit and scope of the present subject matter and without diminishing its intended advantages. It is therefore intended that such changes and modifications be covered by the appended claims.

The invention is claimed as follows:

1. A medical device system comprising:
a cluster including a plurality of nodes, wherein the cluster is configured to run proprietary software that creates a closed configuration for the cluster;
a plurality of medical devices implementing at least some of the nodes, at least one of the nodes being an access node;
a distributed database shared along the cluster and hosted by at least some of the nodes; and
at least one external equipment separate from the cluster, the at least one external equipment running software different than the proprietary software, wherein the different software is unable to directly communicate with the cluster having the closed configuration, and wherein the different software is configured to perform at least one of (i) writing to at least some of the distributed database via the access node or (ii) reading from at least some of the distributed database via the access node.

2. The medical device system of claim 1, wherein the at least one access node is provided separately from the medical devices.

3. The medical device system of claim 1, wherein the at least one access node is provided with one of the medical devices.

4. The medical device system of claim 1, wherein the at least one access node does not host the distributed database.

5. The medical device system of claim 1, wherein the at least one external equipment is a first external equipment, wherein the medical device system further includes a virtual access node of the cluster formed via a second external equipment, and wherein the virtual access node provides a secure data exchange environment so as to ensure security of the cluster while operating with the second external equipment.

6. The medical device system of claim 5, wherein the secure data exchange environment includes a secure channel, such as a virtual private network.

7. The medical device system of claim 1, wherein the at least one external equipment is configured to deliver data to the distributed database, and wherein the data is used by one of the medical devices implementing one of the nodes for treatment.

8. The medical device system of claim 1, wherein the plurality of medical devices are of a same treatment type.

9. The medical device system of claim 1, wherein the plurality of medical devices are configured to treat a common patient.

10. The medical device system of claim 1, wherein the distributed database is populated by (i) at least a first subset of the nodes that produce data and push data to other nodes, (ii) a second subset of the nodes hosting the distributed database pulling data from other nodes, or (iii) a combination of (i) and (ii).

11. A medical device system comprising:
a cluster including a plurality of nodes, wherein the cluster is configured to run proprietary software that creates a closed configuration for the cluster;
each of at least a set of the plurality of nodes implemented by at least one of a plurality of medical devices;
a distributed database hosted by each of the plurality of medical devices, at least one first access node configured to also host the distributed database;
at least one second access node provided separately from the distributed database; and
at least one external equipment separate from the cluster, the at least one external equipment running software different than the proprietary software, wherein the different software is unable to directly communicate with the cluster having the closed configuration, and wherein the different software is configured to perform at least one of (i) writing to the distributed database via the at least one first access node or the at least one second access node, or (ii) reading from the distributed database via the at least one first access node or the at least one second access node.

12. The medical device system of claim 11, wherein the at least one first access node and the at least one second access node are located separately from the medical devices.

13. The medical device system of claim 11, wherein the at least one first access node and the at least one second access node are provided with or operate with a user interface.

14. A medical device system comprising:
a cluster including a plurality of nodes, wherein the cluster is configured to run proprietary software that creates a closed configuration for the cluster;
a plurality of medical devices implementing at least at least some of the nodes, at least one of the nodes being an access node including an external part and an internal part;
a distributed database provided along the cluster and hosted by at least some of the nodes, the distributed database, when stored by the at least one access node, associated with the internal part of the access node; and
at least one external equipment separate from the cluster, the at least one external equipment running software different than the proprietary software, wherein the different software is unable to directly communicate with the cluster having the closed configuration, and wherein the different software is configured to perform at least one of (i) writing to at least some of the distributed database via the external part of the access node or (ii) reading from at least some of the distributed database via the external part of the access node.

15. The medical device system of claim 14, wherein the external part and the internal part are separated by a processing and memory manager configured to (i) provide data to the external part coming from the internal part and (ii) provide data to the internal part coming from the external part.

16. A medical device system comprising:
a cluster including a plurality of nodes, wherein the cluster is configured to run first software that creates a closed configuration for the cluster;
a plurality of medical devices implementing at least some of the nodes, each medical device including a first processor and a memory configured to perform a medical procedure; and
a distributed database shared along the cluster by at least some of the nodes, the distributed database deployed on the plurality of medical devices, the distributed database separated from the first processor and memory configured to perform the medical procedure by a second processor and a memory manager running second software different than the first software, wherein the second software is unable to directly communicate with the cluster having the closed configuration, and wherein the second software is configured to (i) provide, to the first processor and memory, data coming from the distributed database and (ii) provide, to the distributed database, data coming from the first processor and memory.

17. The medical device system of claim 16, wherein the first processor and memory are configured to initiate communication with the distributed database via the second processor and the memory manager.

18. The medical device system of claim 16, wherein the distributed database is located in a cluster control part of the medical device that is separate from the first processor and memory located in a therapy control part of the medical device, the cluster control part separated from the therapy control part by the second processor and the memory manager.

19. A medical device system comprising:
a cluster including a plurality of nodes, wherein the cluster is configured to run first software that creates a closed configuration for the cluster;
a plurality of medical devices implementing at least some of the nodes;
a distributed data base shared along the cluster and hosted by the plurality of medical devices;
an external equipment separate from the cluster; and
a virtual access node of the cluster formed with the external equipment and one of the medical devices, the virtual access node providing a secure data exchange environment so as to ensure security of the distributed database, the virtual access node running second software different than the first software, wherein the second software is unable to directly communicate with the cluster having the closed configuration, and wherein the second software (i) writes to the medical device or (ii) reads from the medical device.

20. The medical device system of claim 19, wherein the medical device includes a first virtual access node interface and the external equipment includes a second virtual access node interface, and wherein the secure data exchange environment includes a secure channel such as a virtual private network interfacing with the virtual access node interfaces.

* * * * *